(12) United States Patent
Carter

(10) Patent No.: US 6,613,790 B2
(45) Date of Patent: Sep. 2, 2003

(54) PRODRUGS OF COX-2 INHIBITORS

(75) Inventor: Jeffery S. Carter, Chesterfield, MO (US)

(73) Assignee: Pharmacia Corporation, St. Louis, MO (US)

(*) Notice: Subject to any disclaimer, the term of this patent is extended or adjusted under 35 U.S.C. 154(b) by 0 days.

(21) Appl. No.: 10/123,730

(22) Filed: Apr. 16, 2002

(65) Prior Publication Data

US 2003/0055012 A1 Mar. 20, 2003

Related U.S. Application Data

(60) Provisional application No. 60/357,959, filed on Feb. 19, 2002, and provisional application No. 60/284,589, filed on Apr. 17, 2001.

(51) Int. Cl.[7] ............... A61K 31/415; L01D 231/12

(52) U.S. Cl. ...................... 514/406; 548/377.1

(58) Field of Search ............... 548/377.1; 514/406

(56) References Cited

U.S. PATENT DOCUMENTS

| | | | |
|---|---|---|---|
| 3,644,449 A | 2/1972 | Murphy et al. | 260/513 |
| 3,647,858 A | 3/1972 | Hinkley et al. | 260/470 |
| 3,707,475 A | 12/1972 | Lombardino et al. | 260/309 |
| 3,901,908 A | 8/1975 | Fitzi et al. | 260/309 |
| 3,984,431 A | 10/1976 | Gueremy et al. | 260/310 |
| 4,011,328 A | 3/1977 | Pinhas et al. | 424/263 |
| 4,051,250 A | 9/1977 | Dahm et al. | 424/272 |
| 4,146,721 A | 3/1979 | Rainer | 548/374 |
| 4,302,461 A | 11/1981 | Cherkofsky | 424/263 |
| 4,372,964 A | 2/1983 | Whitney | 424/273 |
| 4,381,311 A | 4/1983 | Haber | 424/275 |
| 4,427,693 A | 1/1984 | Haber | 424/275 |
| 4,472,422 A | 9/1984 | Whitney | 424/273 |
| 4,503,065 A | 3/1985 | Wilkerson | 514/396 |
| 4,533,666 A | 8/1985 | Matsumoto et al. | 514/277 |
| 4,576,958 A | 3/1986 | Wexler | 514/400 |
| 4,590,205 A | 5/1986 | Haber | 514/438 |
| 4,632,930 A | 12/1986 | Carini et al. | 514/365 |
| 4,686,231 A | 8/1987 | Bender et al. | 514/333 |
| 4,820,827 A | 4/1989 | Haber | 549/78 |
| 4,822,805 A | 4/1989 | Takasugi et al. | 514/341 |
| 4,914,121 A | 4/1990 | Sawai et al. | 514/406 |
| 5,051,518 A | 9/1991 | Murray et al. | 548/373 |
| 5,134,142 A | 7/1992 | Matsuo et al. | 514/255 |
| 5,169,857 A | 12/1992 | Angerbauer et al. | 514/344 |
| 5,338,749 A | 8/1994 | Wuest et al. | 514/364 |
| 5,344,991 A | 9/1994 | Reitz et al. | 568/34 |
| 5,380,738 A | 1/1995 | Norman et al. | 514/374 |
| 5,387,592 A | 2/1995 | Bradbury et al. | 514/312 |
| 5,389,635 A | 2/1995 | Olson | 514/255 |
| 5,393,790 A | 2/1995 | Reitz et al. | 514/709 |
| 5,401,765 A | 3/1995 | Lee | 548/406 |
| 5,434,178 A | 7/1995 | Talley et al. | 514/406 |
| 5,486,534 A | 1/1996 | Lee et al. | 514/406 |
| 5,932,598 A | * 8/1999 | Talley et al. | 514/341 |
| 6,436,967 B1 | * 8/2002 | Talley et al. | 514/341 |

FOREIGN PATENT DOCUMENTS

| | | | |
|---|---|---|---|
| EP | 0026928 | 1/1984 | ......... C07D/261/08 |
| EP | 0372445 | 3/1994 | ......... C07D/233/64 |
| EP | 0799823 | 10/1997 | ......... C07D/207/32 |
| EP | 0592664 | 7/2000 | ......... C07D/277/44 |
| JP | 1045374 | 2/1989 | ......... C07D/257/04 |
| JP | 4277724 | 10/1992 | ............. G02F/1/35 |
| JP | 5323522 | 12/1993 | ............. G03C/5/29 |
| WO | WO9205162 | 4/1992 | ......... C07D/261/08 |
| WO | WO9219604 | 11/1992 | ......... C07D/261/08 |
| WO | WO9314082 | 7/1993 | ......... C07D/401/04 |

OTHER PUBLICATIONS

H. Faid–Allah et al. *Ind. J. Chem*, 27, 245 (1988).
D. Mukerjee et al. *Acta. Pharma. Jugosl.*, 31, 151 (1981).
T. Ivanov *Mh. Chem.*, 97, 1499 (1966).
J. Larsen et al. *Int. J. Pharmaceutics*, 37, 87, (1987).
J. Larsen et al. *Int. J. Pharmaceutics*, 47, 103 (1988).
Horng–Chih Huang et al. *Tet. Lett.*, 35, 7201–04 (1994).
M.R. Grimmett, "Advances in Imidazole Chemistry" in Advances in Heterocyclic Chemistry, 12, 104 (1970).
Suzuki et al. *Synth. Commun.*, 11, 513, (1981).
*J. Org. Chem.* 57, 2195, (1992).
Talley et al., N–[[(5–Methy–3–phenylisoxzol–4–yl)–phenyl]sulfonyl]propanamide, Sodium Salt Parecoxib Sodium: A Potent and Selective Inhibitor of COX–2 for Parenteral Administration, *J. Med. Chem.*, vol. 43, pp. 1661–1663 (2000).
Khanna et al., 1,2–Diarylphyrroles as Potent and Selective Inhibitors of Cyclooxygenase–2, *J. Med. Chem.* vol. 40, pp. 1619–1633 (1997).
Penning et al., Synthesis and Biological Evaluation of the 1,5–Diarylpyrazole Class of Cyclooxygenase–2 Inhibitors: Identification of 4–[5–(4–Methylphenyl)–3–(trifluoromethyl)–1H–Pyrazol–1–yl]benzenesulfonamide (SC–58635, Celecoxib), *J. Med. Chem.*, vol. 40, pp. 1347–1365 (1997).

(List continued on next page.)

*Primary Examiner*—Joseph K. McKane
*Assistant Examiner*—Kamal Saeed
(74) *Attorney, Agent, or Firm*—David B. Fournier; Kalim S. Fuzail

(57) ABSTRACT

A compound of Formula (I), or a pharmaceutically-acceptable salt thereof, suitable for use in the treatment of a cyclooxygenase-2 mediated disease is provided.

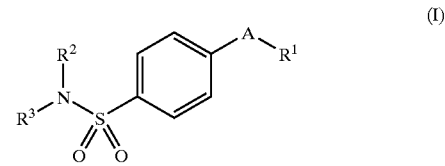

(I)

Also provided is a pharmaceutical composition comprising a compound of Formula (I), or a pharmaceutically-acceptable salt thereof, and a method for treatment of a cyclooxygenase-2 mediated disease by administering to a subject in need thereof a therapeutically-effective amount of the pharmaceutical composition.

12 Claims, No Drawings

FOREIGN PATENT DOCUMENTS

| | | | |
|---|---|---|---|
| WO | WO9413635 | 6/1994 | ......... C07D/323/49 |
| WO | WO9415932 | 7/1994 | ......... C07D/333/18 |
| WO | WO9420480 | 9/1994 | ......... C07D/277/36 |
| WO | WO9426731 | 11/1994 | ......... C07D/333/18 |
| WO | WO9427980 | 12/1994 | ......... C07D/263/32 |
| WO | WO9500501 | 1/1995 | ......... C07D/277/02 |
| WO | WO9510508 | 4/1995 | ......... C07D/263/38 |
| WO | WO9515316 | 6/1995 | ......... C07D/231/12 |
| WO | WO6903392 | 2/1996 | ......... C07D/277/26 |
| WO | WO9603388 | 2/1996 | ......... C07D/233/54 |
| WO | WO9619462 | 6/1996 | ......... C07D/263/32 |
| WO | WO9719068 | 5/1997 | ......... C07D/295/08 |
| WO | WO9727174 | 7/1997 | ......... C07C/311/00 |
| WO | WO9734882 | 9/1997 | ......... C07D/263/38 |
| WO | WO9738986 | 10/1997 | ......... C07D/261/08 |
| WO | WO9744333 | 11/1997 | ......... C07D/271/06 |
| WO | WO9825597 | 6/1998 | .......... A61K/31/00 |
| WO | WO9914205 | 3/1999 | ......... C07D/263/38 |
| WO | WO9920606 | 4/1999 | ......... C07D/211/00 |
| WO | WO9923150 | 5/1999 | .......... C08K/5/203 |
| WO | WO9962884 | 12/1999 | ......... C07D/231/06 |
| WO | WO0026216 | 5/2000 | ......... C07D/471/04 |
| WO | WO0038730 | 7/2000 | .......... A61K/45/06 |
| WO | WO0038786 | 7/2000 | .......... A61P/41/00 |
| WO | WO0061571 | 10/2000 | ......... C07D/307/32 |
| WO | WO0063194 | 10/2000 | ......... C07D/271/06 |
| WO | WO0100229 | 1/2001 | .......... A61K/38/19 |
| WO | WO0115687 | 3/2001 | .......... A61K/31/18 |
| WO | WO0116138 | 3/2001 | ......... C07D/498/04 |
| WO | WO01/28548 | 4/2001 | .......... A61K/31/16 |
| WO | WO0145683 | 6/2001 | .......... A61K/31/00 |
| WO | WO0145698 | 6/2001 | .......... A61K/31/27 |
| WO | WO0156555 | 8/2001 | .......... A61K/31/00 |
| WO | WO0156573 | 8/2001 | ......... A61K/31/445 |
| WO | WO0183461 | 11/2001 | ......... C07D/263/30 |
| WO | WO0183463 | 11/2001 | ......... C07D/217/06 |
| WO | WO0183464 | 11/2001 | ......... C07D/271/06 |
| WO | WO0196308 | 12/2001 | ......... C07D/213/64 |
| WO | WO0205799 | 1/2002 | .......... A61K/31/00 |
| WO | WO0209759 | 2/2002 | .......... A61K/45/06 |
| WO | WO0217923 | 3/2002 | ......... A61K/31/535 |

OTHER PUBLICATIONS

Liao et al., New Selective and Potent 5–Ht $_{1B-1D}$ Antagonists: Chemistry and Pharmalogical Evaluation of N–Piperazinylphenyl Biphenylcarboxamides and Biphenylsulfonamides, *J. Med. Chem.*, vol. 43, pp. 517–525 (2000).

Cremlyn et al., Chlorosulfonation of N–Phenylmorpholine, Benzothiazole, 2–Methyl Benzothiazole and Triphenyloxazole, *Phosphorus, Sulfur, and Silocon*, vol. 73, pp. 107–120 (1992).

De Vleeschauwer et al. Remarkably Mild and Simple Preparations of Sulfinates, Sulfonyl Chlorides and Sulfonamides from Thioanisoles, Synlettt, pp. 375–377 (1997).

Hellwinkel et al. Heterocyclensynthesen mit MF/Al$_2$ O$_3$ – Basensystemen: 2–Arylbenzofurane und 2,3–Diarylisochinolin–1(2H)–one, Synthesis, pp. 1135–1141 (1995).

Reid et al., Notiz zur Dehydrierung von Delta 2–Pyrazolinen mit N–Bromsuccinimid, *Chemische Berichte*, pp. 378–379 (1969).

Peet et al., Factors Which Influence the Formation of Oxadiazoles From Anthranilhydrazides and Other Benzoylhydrazines, *J. Heterocyclic Chem.*, vol. 21, pp. 1807–1816 (1984).

* cited by examiner

PRODRUGS OF COX-2 INHIBITORS

This application claims priority of U.S. provisional patent application Ser. No. 60/284,589 filed on Apr. 17, 2001, and of U.S. provisional patent application Ser. No. 60/357,959 filed on Feb. 19, 2002.

FIELD OF THE INVENTION

This invention is in the field of antiinflammatory pharmaceutical agents and specifically relates to prodrugs of compounds which selectively inhibit cyclooxygenase-2.

BACKGROUND OF THE INVENTION

The use of non-steroidal antiinflammatory drugs (NSAIDs) in treating pain and the swelling associated with inflammation also produce severe side effects, including life threatening ulcers. The recent discovery of an inducible enzyme associated with inflammation ("prostaglandin G/H synthase II" or "cyclooxygenase-2 (COX-2)") provides a viable target of inhibition which more effectively reduces inflammation and produces fewer and less drastic side effects.

Compounds which selectively inhibit cyclooxygenase-2 have been described. U.S. Pat. No. 5,380,738 and WO94/27980 describe oxazoles which selectively inhibit cyclooxygenase-2. U.S. Pat. No. 5,344,991 describes cyclopentenes which selectively inhibit cyclooxygenase-2. U.S. Pat. No. 5,393,790 describes spiro compounds which selectively inhibit cyclooxygenase-2. WO94/15932 describes thiophene and furan derivatives which selectively inhibit cyclooxygenase-2. WO94/13635 and WO94/20480 describe compounds which selectively inhibit cyclooxygenase-2. WO95/15316 describes pyrazolyl sulfonamide derivatives which selectively inhibit cyclooxygenase-2. However, in some circumstances, prodrugs of antiinflammatory compounds are advantageous, especially where the prodrugs have increased water solubility or delayed onset of action.

Substituted sulfonamides have been described. Pyrazolyl-sulfonylureas have been described as having possible hypoglycemic activity [H. Faid-Allah and H. Mokhtar, *Ind. J. Chem*, 27, 245 (1988)]. JP 1,045,374 describes water soluble tetrazolium compounds useful in assays for determining reducing substances. D. Mukerjee et. al. [*Acta. Pharma. Jugosl.*, 31, 151 (1981)] describe tetrazolium sulfonamides as antiviral agents. JP 4,277,724 describes triphenyl pyrazolines as nonlinear optical material. JP 5,323,522 describes the use of heterocyclic compounds in black and white photographic material. U.S. Pat. No. 5,389,635 describes substituted imidazoles as angiotensin II antagonists. U.S. Pat. No. 5,387,592 describes substituted benzimidazole derivatives as angiotensin II antagonists. G. Dorofeenko et. al. [*Khim. Fann. Zh.*, 16, 920 (1982)] describe pyridinium salts as antiviral agents. U.S. Pat. No. 5,338,749 describes diaryl-substituted heterocyclyl compounds as anti-arthritis agents. WO94/26731 describes thiophene compounds which selectively inhibit cyclooxygenase-2. WO95/00501 describes compounds which selectively inhibit cyclooxygenase-2, and specifically, 3-(4-(trifluoroacetylaminosulfonyl)phenyl)-2-(4-fluorophenyl) thiophene is described. T. Ivanov [*Mh. Chem.*, 97, 1499 (1966)] describes the preparation of diarylindone derivatives as possible indicators, and 2-(4-(N-methylaminosulfonyl) phenyl)-3-phenylindone is specifically described.

J. Larsen and H. Bundgaard [*Int. J. Pharmaceutics*, 37, 87 (1987)] describe the evaluation of N-acylsulfonamides as potential prodrug derivatives. J. Larsen et. al. [*Int. J. Pharmaceutics*, 47, 103 (1988)] describe the evaluation of N-methylsulfonamides as potential prodrug derivatives.

There currently exists a need for compounds suitable for use in antiinflammatory compositions which can readily penetrate across biological membranes to provide improved drug absorption. Further, there currently exists a need for compounds which are more soluble and stable. The compounds of the present invention are found to show usefulness as prodrugs.

SUMMARY OF THE INVENTION

The present invention provides a compound of Formula (I):

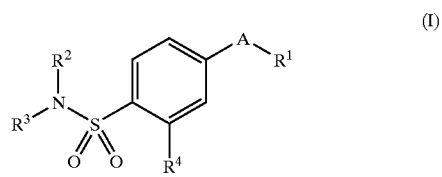

or a pharmaceutically-acceptable salt thereof wherein:

A is a ring substituent selected from the group consisting of heterocyclyl, heteroaryl, cycloalkenyl and aryl, wherein A is optionally substituted at a substitutable position with one or more radicals independently selected at each occurrence from the group consisting of alkylcarbonyl, formyl, halo, alkyl, haloalkyl, oxo, cyano, nitro, carboxyl, alkoxy, aminocarbonyl, alkoxycarbonyl, carboxyalkyl, cyanoalkyl, hydroxyalkyl, haloalkylsulfonyloxy, alkoxyalkyloxyalkyl, carboxyalkoxyalkyl, cycloalkylalkyl, alkenyl, alkynyl, heterocyclyloxy, alkylthio, cycloalkyl, aryl, heterocyclyl, cycloalkenyl, aralkyl, heterocyclylalkyl, alkylthioalkyl, arylcarbonyl, aralkylcarbonyl, aralkenyl, alkoxyalkyl, arylthioalkyl, aryloxyalkyl, aralkylthioalkyl, aralkoxyalkyl, alkoxycarbonylalkyl, aminocarbonylalkyl, alkylaminocarbonyl, N-arylaminocarbonyl, N-alkyl-N-arylaminocarbonyl, alkylaminocarbonylalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl and N-alkyl-N-arylaminosulfonyl;

$R^1$ is selected from the group consisting of heteroaryl, heterocyclyl, cycloalkyl, cycloalkenyl and aryl, wherein $R^1$ is optionally substituted at a substitutable position with one or more radicals independently selected at each occurrence from the group consisting of alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

$R^2$ and $R^3$ are independently selected from the group consisting of hydrido, alkyl, alkylcarbonyl, hydroxyalkyl, heterocyclyl, heteroaryl, monosaccharide, disaccharide, polysaccharide, alkylphosphate, acyloxyalkyl, alkylaminocarbonyl, alkoxyaralkyl and carboxyalkyl, wherein $R^3$ is optionally substituted at a substitutable position with one or more radicals independently selected at each occurrence from the group consisting of alkylcarbonyl, formyl, halo, alkyl, haloalkyl, oxo, cyano, nitro, carboxyl, alkoxy, aminocarbonyl, alkoxycarbonyl, carboxyalkyl, cyanoalkyl, hydroxyalkyl, haloalkylsulfonyloxy, alkoxyalkyloxyalkyl, carboxyalkoxyalkyl, cycloalkylalkyl, alkenyl, alkynyl, heterocyclyloxy, alkylthio, cycloalkyl, aryl, heterocyclyl, cycloalkenyl, aralkyl, heterocyclylalkyl, alkylthioalkyl, arylcarbonyl, aralkylcarbonyl, aralkenyl, alkoxyalkyl, arylthioalkyl, aryloxyalkyl, aralkylthioalkyl, aralkoxyalkyl, alkoxycarbonylalkyl, aminocarbonylalkyl, alkylaminocarbonyl, N-arylaminocarbonyl, N-alkyl-N-arylaminocarbonyl, alkylaminocarbonylalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, and N-alkyl-N-arylaminosulfonyl;

wherein at least one of $R^2$ and $R^3$ is other than hydrido;

wherein $R^2$ is other than alkyl, carboxyalkyl or alkylcarbonyl when $R^3$ is hydrido; and wherein $R^3$ is other than alkyl, carboxyalkyl or alkylcarbonyl when $R^2$ is hydrido;

or, $R^2$ and $R^3$ are taken together along with the nitrogen to which they are attached to form a three to seven membered saturated, partially unsaturated or unsaturated heterocyclic ring and may optionally be substituted at a substitutable position with one or more $R^5$ radicals, wherein the $R^5$ radicals are independently selected at each occurrence from the group consisting of alkylcarbonyl, formyl, halo, alkyl, haloalkyl, alkylphosphate, phosphate, oxo, cyano, nitro, alkoxy, aminocarbonyl, alkoxycarbonyl, carboxyalkyl, cyanoalkyl, hydroxyalkyl, haloalkylsulfonyloxy, alkoxyalkyloxyalkyl, carboxyalkoxyalkyl, cycloalkylalkyl, alkenyl, alkynyl, heterocyclyloxy, alkylthio, cycloalkyl, aryl, heterocyclyl, cycloalkenyl, aralkyl, heterocyclylalkyl, alkylthioalkyl, arylcarbonyl, aralkylcarbonyl, aralkenyl, alkoxyalkyl, arylthioalkyl, aryloxyalkyl, aralkylthioalkyl, aralkoxyalkyl, alkoxycarbonylalkyl, aminocarbonylalkyl, alkylaminocarbonyl, N-arylaminocarbonyl, N-alkyl-N-arylaminocarbonyl, alkylaminocarbonylalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl and N-alkyl-N-arylaminosulfonyl; and $R^4$ is selected from hydrido and fluoro;

wherein $R^5$ is other than methyl when A is isoxazole, $R^1$ is phenyl and $R^2$ and $R^3$ are taken together to form a pyrrole ring.

The present invention also provides a pharmaceutical composition comprising a therapeutically-effective amount of a compound of Formula (I), and a method of treating a cyclooxygenase-2 mediated disease such as inflammation or an inflammation-related disorder in a subject.

DETAILED DESCRIPTION OF THE INVENTION

Compounds of Formula (I) would be useful for, but not limited to, the treatment of inflammation in a subject, and for treatment of other cyclooxygenase-2 mediated disorders, such as, as an analgesic in the treatment of pain and headaches, or as an antipyretic for the treatment of fever. For example, compounds of the invention would be useful to treat arthritis, including but not limited to rheumatoid arthritis, spondyloarthropathies, gouty arthritis, osteoarthritis, systemic lupus erythematosus and juvenile arthritis. Such compounds of the invention would be useful in the treatment of asthma, bronchitis, menstrual cramps, premature labor, tendinitis, bursitis, skin-related conditions such as psoriasis, eczema, bums and dermatitis, and from post-operative inflammation including from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis. Compounds of the invention would be useful for the prevention or treatment of cancer, such as colorectal cancer, and cancer of the breast, lung, prostate, bladder, cervix and skin. Compounds of the invention would be useful in treating inflammation in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as retinitis, retinopathies, uveitis, ocular photophobia, and of acute injury to the eye tissue. The compounds would also be useful in the treatment of pulmonary inflammation, such as that associated with viral infections and cystic fibrosis. The compounds would also be useful for the treatment of certain central nervous system disorders, such as cortical dementias including Alzheimer's disease, and central nervous system damage resulting from stroke, ischemia and trauma. The compounds of the invention are useful as anti-inflammatory agents, such as for the treatment of arthritis, with the additional benefit of having significantly less harmful side effects. These compounds would also be useful in the treatment of allergic rhinitis, respiratory distress syndrome, endotoxin shock syndrome, and atherosclerosis. The compounds would also be useful in the treatment of pain, but not limited to postoperative pain, dental pain, muscular pain, and pain resulting from cancer. The compounds would be useful for the prevention of dementias, such as Alzheimer's disease.

Besides being useful for human treatment, these compounds are also useful for veterinary treatment of companion animals, exotic animals and farm animals, including mammals, rodents, and the like. More preferred animals include horses, dogs, and cats.

The present compounds may also be used in co-therapies, partially or completely, in place of other conventional antiinflammatories, such as together with steroids, NSAIDs, 5-lipoxygenase inhibitors, $LTB_4$ antagonists and $LTA_4$ hydrolase inhibitors.

Suitable $LTB_4$ inhibitors include, among others, ebselen, Bayer Bay-x-1005, Ciba Geigy compound CGS-25019C, Leo Denmark compound ETH-615, Lilly compound LY-293111, Ono compound ONO-4057, Terumo compound TMK-688, Lilly compounds LY-213024, 264086 and 292728, ONO compound ONO-LB457, Searle compound SC-53228, calcitrol, Lilly compounds LY-210073, LY223982, LY233469, and LY255283, ONO compound ONO-LB-448, Searle compounds SC-41930, SC-50605 and SC-51146, and SK&F compound SKF-104493. Preferably, the LTB4 inhibitors are selected from ebselen, Bayer Bay-x-1005, Ciba Geigy compound CGS-25019C, Leo Denmark compound ETH-615, Lilly compound LY-293111, Ono compound ONO-4057, and Terumo compound TMK-688.

Suitable 5-LO inhibitors include, among others, masoprocol, tenidap, zileuton, pranlukast, tepoxalin, rilopirox, flezelastine hydrochloride, enazadrem phosphate, and bunaprolast.

The present compounds may also be used in combination therapies with opioids and other analgesics, such as morphine, meperidine or codeine.

The present invention may also be used in combination with a 5-hydroxytriptamine (5-HT) receptor agonist. Amino compounds such as, for example but not limited to, sumatriptan, zolmitriptan, naratriptan, rizatriptan, eletriptan, almotriptan, frovatriptan, ergotamine, dihydroergotamine.

The term "cyclooxygenase-2 inhibitor" embraces compounds which selectively inhibit cyclooxygenase-2 over cyclooxygenase-1. Preferably, the compounds have a cyclooxygenase-2 $IC_{50}$ of less than about 0.5 $\mu M$, and also have a selectivity ratio of cyclooxygenase-2 inhibition over cyclooxygenase-1 inhibition of at least 50, and more preferably of at least 100. Even more preferably, the compounds have a cyclooxygenase-1 $IC_{50}$ of greater than about 1 $\mu M$, and more preferably of greater than 20 $\mu M$. Such preferred selectivity may indicate an ability to reduce the incidence of common NSAID-induced side effects.

The phrase "therapeutically-effective" is intended to qualify the amount of each agent for use in the combination therapy which will achieve the goal of improvement in severity and the frequency of incidence over treatment of each agent by itself, while avoiding adverse side effects typically associated with alternative therapies.

The phrase "combination therapy" (or "co-therapy"), in defining use of a cyclooxygenase-2 inhibitor agent and another agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

The term "prodrug" refers to compounds which are drug precursors which, following administration to a subject and subsequent absorption, is converted to an active species in vivo via some process, such as a metabolic process. Other products from the conversion process are easily disposed of by the body. More preferred prodrugs produce products from the conversion process which are generally accepted as safe.

In one embodiment, compounds which inhibit cyclooxygenase-2 consists of compounds of Formula (I) wherein A is selected from partially unsaturated heterocyclyl, 5- or 6-membered heteroaryl, lower cycloalkenyl and phenyl, wherein A is optionally substituted at a substitutable position with one or more radicals independently selected at each occurence from formyl, lower alkylcarbonyl, halo, lower alkyl, lower haloalkyl, oxo, cyano, nitro, carboxyl, lower alkoxy, aminocarbonyl, lower alkoxycarbonyl, lower carboxyalkyl, lower cyanoalkyl, lower hydroxyalkyl, lower haloalkylsulfonyloxy, lower alkoxyalkyloxyalkyl, lower carboxyalkoxyalkyl, lower cycloalkylalkyl, lower alkenyl, lower alkynyl, heterocyclyloxy, lower alkylthio, lower cycloalkyl, phenyl, 5–6 membered heterocyclyl, lower cycloalkenyl, lower phenylalkyl, 5–6 membered heterocyclylalkyl, lower alkylthioalkyl, phenylcarbonyl, lower phenylalkylcarbonyl, lower phenylalkenyl, lower alkoxyalkyl, lower phenylthioalkyl, lower phenyloxyalkyl, lower phenylalkylthioalkyl, lower phenylalkoxyalkyl, lower alkoxycarbonylalkyl, lower aminocarbonylalkyl, lower alkylaminocarbonyl, N-phenylaminocarbonyl, lower N-alkyl-N-phenylaminocarbonyl, lower alkylaminocarbonylalkyl, lower alkylamino, N-phenylamino, lower N-phenylalkylamino, lower N-alkyl-N-phenalkylamino, lower N-alkyl-N-phenylamino, lower aminoalkyl, lower alkylaminoalkyl, lower N-phenylaminoalkyl, lower N-phenalkylaminoalkyl, lower N-alkyl-N-phenalkylaminoalkyl, lower N-alkyl-N-phenylaminoalkyl, phenyloxy, lower phenylalkoxy, lower phenylthio, lower phenalkylthio, lower alkylsulfinyl, lower alkylsulfonyl, aminosulfonyl, lower alkylaminosulfonyl, N-phenylaminosulfonyl, phenylsulfonyl, and lower N-alkyl-N-phenylaminosulfonyl; and $R^1$ is selected from 5- or 6-membered heteroaryl and heterocyclyl, lower cycloalkyl, lower cycloalkenyl and phenyl, where $R^1$ is optionally substituted at a substitutable position with one or more radicals independently selected at each occurence from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio.

In another embodiment, compounds which inhibit cyclooxygenase-2 consists of compounds of Formula (I) wherein A is a radical selected from thienyl, oxazolyl, furyl, pyrrolyl, thiazolyl, imidazolyl, benzofuryl, indenyl, benzothienyl, isoxazolyl, pyrazolyl, cyclopentenyl, cyclopentadienyl, benzindazolyl, benzopyranopyrazolyl, phenyl, and pyridyl, wherein A is optionally substituted at a substitutable position with one or more radicals independently selected at each occurence from formyl, methylcarbonyl, fluoro, chloro, bromo, methyl, trifluoromethyl, difluoromethyl, oxo, cyano, carboxyl, methoxy, aminocarbonyl, methoxycarbonyl, ethoxycarbonyl, carboxypropyl, hydroxymethyl, cyanomethyl, phenyl, phenylmethyl, methoxycarbonyl, phenylcarbonyl, methoxymethyl, phenyloxymethyl, aminocarbonylmethyl, carboxymethyl, and phenyloxy; and $R^1$ is selected from thienyl, oxazolyl, isoxazolyl (heteroaryl was never in claim 1 for this substituent), furyl, thiazolyl, pyridyl, and phenyl, where $R^1$ is optionally substituted at a substitutable position with one or more radicals independently selected at each occurence from methyl, trifluoromethyl, hydroxyl, hydroxymethyl, trifluoromethoxy, nitro, methoxymethyl, fluoro, chloro, bromo, methoxy and methylthio.

In yet another embodiment, A is other than tetrazolium or pyridinium. In still another embodiment, A is other than indanone when $R^3$ is carboxyalkyl.

A family of specific compounds of particular interest within Formula (I) consists of compounds and pharmaceutically-acceptable salts thereof as follows:

1-{[4-(5-methyl-3-phenylisoxazol-4-yl)phenyl]sulfonyl}-L-proline;

sodium 1-{[4-(5-methyl-3-phenylisoxazol-4-yl)phenyl]sulfonyl}-L-prolinate;

and methyl 1-{[4-(5-methyl-3-phenylisoxazol-4-yl)phenyl]sulfonyl}-L-prolinate.

Within Formula (I) there is a subclass of compounds of high interest represented by Formula (II):

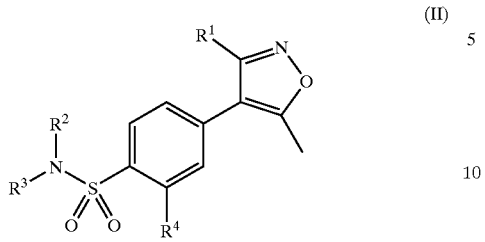

Another subclass of compounds of high interest within Formula (I) are compounds represented by Formula (III):

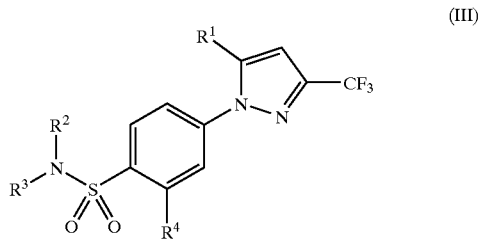

or a pharmaceutically-acceptable salt thereof wherein:
  $R^1$ is selected from heteroaryl, heterocyclyl, cycloalkyl, cycloalkenyl and aryl, wherein $R^1$ is optionally substituted at a substitutable position with one or more radicals indepedently selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;
  $R^2$ and $R^3$ are independently selected from the group consisting of hydrido, alkyl, alkylcarbonyl, hydroxyalkyl, heterocyclyl, heteroaryl, monosaccharide, disaccharide, polysaccharide, alkylphosphate, acyloxyalkyl, alkylaminocarbonyl, alkoxyaralkyl and carboxyalkyl, wherein $R^3$ is optionally substituted at a substitutable position with one or more radicals independently selected at each occurrence from the group consisting of alkylcarbonyl, formyl, halo, alkyl, haloalkyl, oxo, cyano, nitro, carboxyl, alkoxy, aminocarbonyl, alkoxycarbonyl, carboxyalkyl, cyanoalkyl, hydroxyalkyl, haloalkylsulfonyloxy, alkoxyalkyloxyalkyl, carboxyalkoxyalkyl, cycloalkylalkyl, alkenyl, alkynyl, heterocyclyloxy, alkylthio, cycloalkyl, aryl, heterocyclyl, cycloalkenyl, aralkyl, heterocyclylalkyl, alkylthioalkyl, arylcarbonyl, aralkylcarbonyl, aralkenyl, alkoxyalkyl, arylthioalkyl, aryloxyalkyl, aralkylthioalkyl, aralkoxyalkyl, alkoxycarbonylalkyl, aminocarbonylalkyl, alkylaminocarbonyl, N-arylaminocarbonyl, N-alkyl-N-arylaminocarbonyl, alkylaminocarbonylalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, and N-alkyl-N-arylaminosulfonyl; and
  $R^4$ is selected from hydrido and fluoro;
  wherein at least one of $R^2$ and $R^3$ is other than hydrido;
  wherein $R^2$ is other than alkyl, carboxyalkyl or alkylcarbonyl when $R^3$ is hydrido; and
  wherein $R^3$ is other than alkyl, carboxyalkyl or alkylcarbonyl when $R^2$ is hydrido.

A family of specific compounds of particular interest within Formulae (I) and (II) consists of compounds and pharmaceutically-acceptable salts thereof as follows:
  N,N-dimethyl-4-(5-methyl-3-phenylisoxazol-4-yl)benzenesulfonamide; and
  N-ethyl-4-(5-methyl-3-phenylisoxazol-4-yl)-N-propionylbenzenesulfonamide.

or a pharmaceutically-acceptable salt thereof wherein:
  $R^1$ is selected from heteroaryl, heterocyclyl, cycloalkyl, cycloalkenyl and aryl, wherein $R^1$ is optionally substituted at a substitutable position with one or more radicals indepedently selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;
  $R^2$ and $R^3$ are independently selected from the group consisting of hydrido, alkyl, alkylcarbonyl, hydroxyalkyl, heterocyclyl, heteroaryl, monosaccharide, disaccharide, polysaccharide, alkylphosphate, acyloxyalkyl, alkylaminocarbonyl, alkoxyaralkyl and carboxyalkyl, wherein $R^3$ is optionally substituted at a substitutable position with one or more radicals independently selected at each occurrence from the group consisting of alkylcarbonyl, formyl, halo, alkyl, haloalkyl, oxo, cyano, nitro, carboxyl, alkoxy, aminocarbonyl, alkoxycarbonyl, carboxyalkyl, cyanoalkyl, hydroxyalkyl, haloalkylsulfonyloxy, alkoxyalkyloxyalkyl, carboxyalkoxyalkyl, cycloalkylalkyl, alkenyl, alkynyl, heterocyclyloxy, alkylthio, cycloalkyl, aryl, heterocyclyl, cycloalkenyl, aralkyl, heterocyclylalkyl, alkylthioalkyl, arylcarbonyl, aralkylcarbonyl, aralkenyl, alkoxyalkyl, arylthioalkyl, aryloxyalkyl, aralkylthioalkyl, aralkoxyalkyl, alkoxycarbonylalkyl, aminocarbonylalkyl, alkylaminocarbonyl, N-arylaminocarbonyl, N-alkyl-N-arylaminocarbonyl, alkylaminocarbonylalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, and N-alkyl-N-arylaminosulfonyl; and
  $R^4$ is selected from hydrido and fluoro;
  wherein at least one of $R^2$ and $R^3$ is other than hydrido;
  wherein $R^2$ is other than alkyl, carboxyalkyl or alkylcarbonyl when $R^3$ is hydrido; and
  wherein $R^3$ is other than alkyl, carboxyalkyl or alkylcarbonyl when $R^2$ is hydrido.

A compound of particular interest within Formula (III) is N,N-bis(2-hydroxyethyl)-4-[5-(4-methylphenyl)-3-(trifluoromethyl)-1H-pyrazol-1-yl]benzenesulfonamide.

Another compound of particular interest within Formula (M) is N-(2-hydroxyethyl)$_4$-[5-(4-methylphenyl)-3-(trifluoromethyl)-1H-pyrazol-1-yl]benzenesulfonamide.

In another embodiment, compounds which inhibit cyclooxygenase-2 consists of compounds of Formula (I):

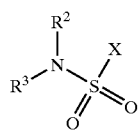

(I)

or a pharmaceutically-acceptable salt thereof wherein:
$R^2$ and $R^3$ are independently selected from the group consisting of hydrido, alkyl, alkylcarbonyl, hydroxyalkyl, heterocyclyl, heteroaryl, monosaccharide, disaccharide, polysaccharide, alkylphosphate, acyloxyalkyl, alkylaminocarbonyl, alkoxyaralkyl and carboxyalkyl, wherein $R^3$ is optionally substituted at a substitutable position with one or more radicals independently selected at each occurrence from the group consisting of alkylcarbonyl, formyl, halo, alkyl, haloalkyl, oxo, cyano, nitro, carboxyl, alkoxy, aminocarbonyl, alkoxycarbonyl, carboxyalkyl, cyanoalkyl, hydroxyalkyl, haloalkylsulfonyloxy, alkoxyalkyloxyalkyl, carboxyalkoxyalkyl, cycloalkylalkyl, alkenyl, alkynyl, heterocyclyloxy, alkylthio, cycloalkyl, aryl, heterocyclyl, cycloalkenyl, aralkyl, heterocyclylalkyl, alkylthioalkyl, arylcarbonyl, aralkylcarbonyl, aralkenyl, alkoxyalkyl, arylthioalkyl, aryloxyalkyl, aralkylthioalkyl, aralkoxyalkyl, alkoxycarbonylalkyl, aminocarbonylalkyl, alkylaminocarbonyl, N-arylaminocarbonyl, N-alkyl-N-arylaminocarbonyl, alkylaminocarbonylalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, and N-alkyl-N-arylaminosulfonyl;
wherein at least one of $R^2$ and $R^3$ is other than hydrido;
wherein $R^2$ is other than alkyl, carboxyalkyl or alkylcarbonyl when $R^3$ is hydrido; and
wherein $R^3$ is other than alkyl, carboxyalkyl or alkylcarbonyl when $R^2$ is hydrido;
or, $R^2$ and $R^3$ are taken together along with the nitrogen to which they are attached to form a three to seven membered saturated, partially unsaturated or unsaturated heterocyclic ring and may optionally be substituted at a substitutable position with one or more $R^5$ radicals, wherein the $R^5$ radicals are independently selected at each occurrence from the group consisting of alkylcarbonyl, formyl, halo, alkyl, haloalkyl, alkylphosphate, phosphate, oxo, cyano, nitro, alkoxy, aminocarbonyl, alkoxycarbonyl, carboxyalkyl, cyanoalkyl, hydroxyalkyl, haloalkylsulfonyloxy, alkoxyalkyloxyalkyl, carboxyalkoxyalkyl, cycloalkylalkyl, alkenyl, alkynyl, heterocyclyloxy, alkylthio, cycloalkyl, aryl, heterocyclyl, cycloalkenyl, aralkyl, heterocyclylalkyl, alkylthioalkyl, arylcarbonyl, aralkylcarbonyl, aralkenyl, alkoxyalkyl, arylthioalkyl, aryloxyalkyl, aralkylthioalkyl, aralkoxyalkyl, alkoxycarbonylalkyl, aminocarbonylalkyl, alkylaminocarbonyl, N-arylaminocarbonyl, N-alkyl-N-arylaminocarbonyl, alkylaminocarbonylalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl and N-alkyl-N-arylaminosulfonyl; and X is any ligand such that when $R^2$ and $R^3$ are hydrido the compound of Formula (I) is a selective COX-2 inhibitor.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical.

Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having two to about twenty carbon atoms and at least one carbon—carbon double bond or, preferably, two to about twelve carbon atoms and at least one carbon—carbon double bond. More preferred alkenyl radicals are "lower alkenyl" radicals having two to about six carbon atoms. The terms "alkenyl" and "lower alkenyl", embrace radicals having "cis" and "trans" orientations, or alternatively, "E" and "Z" orientations. Examples of alkenyl radicals include ethenyl, propenyl, allyl, propenyl, butenyl and 4-methylbutenyl.

The term "alkynyl" denotes linear or branched radicals having at least one carbon—carbon triple bond, and having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about six carbon atoms. Examples of such radicals include propargyl, butynyl, and the like.

The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl.

The term "cycloalkenyl" embraces partially unsaturated carbocyclic radicals having three to twelve carbon atoms. More preferred cycloalkenyl radicals are "lower cycloalkenyl" radicals having four to about eight carbon atoms. Examples of such radicals include cyclobutenyl, cyclopentenyl and cyclohexenyl.

The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having one to six carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl.

The terms "alkoxy" and "alkyloxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy.

The term "alkoxyalkyl" embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide haloalkoxy radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Aryl moieties may also be substituted at a substitutable position with one or more substituents selected independently from alkyl, alkoxyalkyl, alkylaminoalkyl, carboxyalkyl, alkoxycarbonylalkyl, aminocarbonylalkyl, alkoxy, aralkoxy, hydroxyl, amino, halo, nitro, alkylamino, acyl, cyano, carboxy, aminocarbonyl, alkoxycarbonyl and aralkoxycarbonyl.

The term "heterocyclyl" embraces saturated, partially unsaturated and unsaturated heteroatom-containing ring-shaped radicals, where the heteroatoms may be selected from nitrogen, sulfur and oxygen. Examples of saturated heterocyclyl radicals include saturated 3 to 6-membered heteromonocylic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals.

The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like. The term "heteroaryl" also embraces radicals where heterocyclyl radicals are fused with aryl radicals. Examples of such fused bicyclic radicals include benzofuran, benzothiophene, and the like. Said "heterocyclyl group" may have 1 to 3 substituents such as alkyl, hydroxyl, halo, alkoxy, oxo, amino and alkylamino.

The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio.

The term "alkylthioalkyl" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include methylthiomethyl.

The term "alkylsulfinyl" embraces radicals containing a linear or branched alkyl radical, of one to about ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl.

The term "sulfonyl", whether used alone or linked to other terms such as "alkylsulfonyl", denotes a divalent radical, —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide haloalkylsulfonyl radicals.

The terms "sulfamyl", "aminosulfonyl" and "sulfonamidyl" denote NH$_2$O$_2$S—.

The term "acyl" denotes a radical provided by the residue after removal of hydroxyl from an organic acid. Examples of such acyl radicals include alkanoyl and aroyl radicals. Examples of such alkanoyl radicals include formyl, acetyl, propionyl, butyryl, isobutyryl, valeryl, isovaleryl, pivaloyl, hexanoyl, and radicals formed from succinic, glycolic, gluconic, lactic, malic, tartaric, citric, ascorbic, glucuronic, maleic, fumaric, pyruvic, mandelic, pantothenic, β-hydroxybutyric, galactaric and galacturonic acids.

The term "aroyl" embraces aryl radicals with a carbonyl radical as defined below. Examples of aroyl include benzoyl, naphthoyl, phenylacetyl, and the like, and the aryl in said aroyl may be additionally substituted, such as in p-hydroxybenzoyl, and salicylyl.

The term "carbonyl", whether used alone or with other terms, such as "alkoxycarbonyl", denotes —(C=O)—.

The terms "carboxy" or "carboxyl", whether used alone or with other terms, such as "carboxyalkyl", denotes —$CO_2H$. The term "carboxyalkyl" embraces alkyl radicals substituted with a carboxy radical. More preferred are "lower carboxyalkyl" which embrace lower alkyl radicals as defined above, and may be additionally substituted on the alkyl radical with halo. Examples of such lower carboxyalkyl radicals include carboxymethyl, carboxyethyl and carboxypropyl.

The term "alkoxycarbonyl" means a radical containing an alkoxy radical, as defined above, attached via an oxygen atom to a carbonyl radical. More preferred are "lower alkoxycarbonyl" radicals with alkyl portions having one to six carbons. Examples of such lower alkoxycarbonyl (ester) radicals include substituted or unsubstituted methoxycarbonyl, ethoxycarbonyl, propoxycarbonyl, butoxycarbonyl and hexyloxycarbonyl.

The terms "alkylcarbonyl", "arylcarbonyl" and "aralkylcarbonyl" include radicals having alkyl, hydroxylalkyl, aryl, arylalkyl and aryl-hydroxylalkyl radicals, as defined herein, attached to a carbonyl radical. Examples of such radicals include substituted or unsubstituted methylcarbonyl, ethylcarbonyl, propylcarbonyl, butylcarbonyl, pentylcarbonyl, hydroxymethylcarbonyl, hydroxyethylcarbonyl, phenylcarbonyl, benzylcarbonyl, and phenyl(hydroxymethyl)carbonyl.

The term "carboxyalkylcarbonyl" embraces alkylcarbonyl radicals substituted with a carboxy radical. More preferred are "lower carboxyalkylcarbonyl" which embrace lower alkyl radicals as defined above, and may be additionally substituted on the alkyl radical with hydroxyl. Examples of such lower carboxyalkylcarbonyl radicals include carboxymethylcarbonyl, carboxyethylcarbonyl, carboxypropylcarbonyl, $HO_2C(CHOH)_4C(O)$—, $HO_2C(CHOH)_2C(O)$—, $HO_2C(CH_2)(CHOH)C(O)$—, and $HO_2CCH_2C(OH)(CO_2H)C(O)$—.

The term "carboxyalkenylcarbonyl" embraces derivatives of maleic and fumaric acids. Examples of such carboxyalkenylcarbonyl radicals include (Z)-carboxyethenylcarbonyl and (E)-carboxyethenylcarbonyl.

The term "aralkyl" embraces aryl-substituted alkyl radicals such as benzyl, diphenylmethyl, triphenylmethyl, phenylethyl, and diphenylethyl. The aryl in said aralkyl may be additionally substituted with halo, alkyl, alkoxy, halkoalkyl and haloalkoxy. The terms benzyl and phenylmethyl are interchangeable.

The term "heterocyclylalkyl" embraces saturated and partially unsaturated heterocyclyl-substituted alkyl radicals, such as pyrrolidinylmethyl, and heteroaryl-substituted alkyl radicals, such as pyridylmethyl, quinolylmethyl, thienylmethyl, furylethyl, and quinolylethyl. The heteroaryl in said heteroaralkyl may be additionally substituted with halo, alkyl, alkoxy, halkoalkyl and haloalkoxy.

The term "aryloxy" embraces aryl radicals attached through an oxygen atom to other radicals. The term "arylthio" embraces aryl radicals attached to a sulfur atom.

The term "aralkoxy" embraces aralkyl radicals attached through an oxygen atom to other radicals.

The term "heterocyclyloxy" embraces heterocyclyl radicals attached through an oxygen atom to other radicals.

The term "aralkoxyalkyl" embraces aralkoxy radicals attached through an oxygen atom to an alkyl radical.

The term "aralkylthio" embraces aralkyl radicals attached to a sulfur atom. The term "aralkylthioalkyl" embraces aralkylthio radicals attached through a sulfur atom to an alkyl radical.

The term "aminoalkyl" embraces alkyl radicals substituted with amino radicals. More preferred are "lower aminoalkyl" radicals. Examples of such radicals include aminomethyl, aminoethyl, and the like.

The term "alkylamino" denotes amino groups which are substituted with one or two alkyl radicals. Preferred are "lower alkylamino" radicals having alkyl portions having one to six carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "arylamino" denotes amino groups which are substituted with one or two aryl radicals, such as N-phenylamino. The "arylamino" radicals may be further substituted on the aryl ring portion of the radical.

The term "aralkylamino" embraces amino groups which are substituted with one or two aralkyl radicals.

The terms "N-arylaminoalkyl" and "N-aryl-N-alkyl-aminoalkyl" denote aminoalkyl groups which are substituted with one aryl radical or one aryl and one alkyl radical, respectively. Examples of such radicals include N-phenylaminomethyl and N-phenyl-N-methylaminomethyl.

The term "aminocarbonyl" denotes an amide group of the formula —C(=O)$NH_2$. The term "alkylaminocarbonyl" denotes an aminocarbonyl group which has been substituted with one or two alkyl radicals on the amino nitrogen atom. Preferred are "N-alkylaminocarbonyl" and "N,N-dialkylaminocarbonyl" radicals. More preferred are "lower N-alkylaminocarbonyl" and "lower N,N-dialkylaminocarbonyl" radicals with lower alkyl portions as defined above. The term "alkylaminoalkyl" embraces radicals having one or more alkyl radicals attached to an aminoalkyl radical.

The term "aryloxyalkyl" embraces radicals having an aryl radicals attached to an alkyl radical through a divalent oxygen atom.

The term "arylthioalkyl" embraces radicals having an aryl radicals attached to an alkyl radical through a divalent sulfur atom.

The term "monosaccharide" embraces radicals of allose, altrose, arabinose, erythrose, erythrulose, fructose, D-fucitol, L-fucitol, fucosamine, fucose, galactosamine, D-galactosaminitol, galactose, glucosamine, glucosaminitol, glucose, glyceraldehyde, glycerol, glycerone, gulose, idose, lyxose, mannosamine, annose, psicose, quinovose, quinovosamine, rhamnitol, rhamnosamine, rhamnose, ribose, ribulose, sorbose, tagatose, tartaric acid, threose, xylose and xylulose. Further, the term "monosaccharide" also includes modified monosaccharide radicals.

The terms "disaccharide" and "polysaccharide" embrace radicals of abequose, amicetose, amylose, apiose, arcanose, ascarylose, ascorbic acid, boivinose, cellobiose, cellotriose, chacotriose, chalcose, cladinose, colitose, cymarose, 2-deoxyribose, 2-deoxyglucose, diginose, digitalose, digitoxose, evalose, evernitrose, gentianose, gentiobiose, hamamelose, inulin, isolevoglucosenone, isomaltose, isomaltotriose, isopanose, kojibiose, lactose, lactosamine, lactosediamine, laminarabiose, levoglucosan, levoglucosenone, β-maltose, manninotriose, melezitose, melibiose, muramic acid, mycarose, mycinose, neuraminic acid, nigerose, nojirimycin, noviose, oleandrose, panose, paratose, planteose, primeverose, raffinose, rhodinose, rutinose, sarmentose, sedoheptulose, sedoheptulosan, solatriose, sophorose, stachyose, streptose, sucrose, α,α-trehalose, trehalosamine, turanose, tyvelose and umbelliferose. Further, the terms "disaccharide" and "polysaccharide" include modified disaccharide and polysaccharide radicals.

"Amino acid residue" means any of the naturally occurring alpha-, beta- and gamma-amino carboxylic acids, including their D and L optical isomers and racemic mixtures thereof, synthetic amino acids, and derivatives of these natural and synthetic amino acids. The amino acid residue is bonded either through an amino or an acid functional group of the amino acid. The naturally occurring amino acids which can be incorporated in the present invention include, but are not limited to, alanine, arginine, asparagine, aspartic acid, cysteine, glutamic acid, glutamine, glycine, histidine, isoleucine, leucine, lysine, methionine, ornithine, phenylalanine, proline, serine, threonine, cyclohexylalanine, tryptophan, tyrosine, valine, β-alanine, and γ-aminobutyric acid. Derivatives of amino acids which can be incorporated in the present invention include, but are not limited to amino acids having protected and modified carboxylic acids, including acid esters and amides, protected amines, and substituted phenyl rings, including but not limited to alkyl, alkoxy and halo substituted tyrosine and phenylalanine.

The present invention further provides a pharmaceutical composition comprising a therapeutically-effective amount of a compound of Formula (I) in association with at least one pharmaceutically-acceptable carrier, adjuvant or diluent.

The present invention also provides a method of treating a cyclooxygenase-2 mediated disease in a subject comprising the step of administering to the subject a pharmaceutical composition comprising a therapeutically-effective amount of a compound of Formula (I):

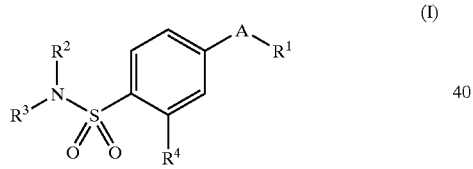

(I)

or a pharmaceutically-acceptable salt thereof wherein:
A is a ring substituent selected from the group consisting of heterocyclyl, heteroaryl, cycloalkenyl and aryl, wherein A is optionally substituted at a substitutable position with one or more radicals independently selected at each occurrence from the group consisting of alkylcarbonyl, formyl, halo, alkyl, haloalkyl, oxo, cyano, nitro, carboxyl, alkoxy, aminocarbonyl, alkoxycarbonyl, carboxyalkyl, cyanoalkyl, hydroxyalkyl, haloalkylsulfonyloxy, alkoxyalkyloxyalkyl, carboxyalkoxyalkyl, cycloalkylalkyl, alkenyl, alkynyl, heterocyclyloxy, alkylthio, cycloalkyl, aryl, heterocyclyl, cycloalkenyl, aralkyl, heterocyclylalkyl, alkylthioalkyl, arylcarbonyl, aralkylcarbonyl, aralkenyl, alkoxyalkyl, arylthioalkyl, aryloxyalkyl, aralkylthioalkyl, aralkoxyalkyl, alkoxycarbonylalkyl, aminocarbonylalkyl, alkylaminocarbonyl, N-arylaminocarbonyl, N-alkyl-N-arylaminocarbonyl, alkylaminocarbonylalkyl, alkyl amino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl and N-alkyl-N-arylaminosulfonyl;

$R^1$ is selected from the group consisting of heteroaryl, heterocyclyl, cycloalkyl, cycloalkenyl and aryl, wherein $R^1$ is optionally substituted at a substitutable position with one or more radicals independently selected at each occurrence from the group consisting of alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

$R^2$ and $R^3$ are independently selected from the group consisting of hydrido, alkyl, alkylcarbonyl, hydroxyalkyl, heterocyclyl, heteroaryl, monosaccharide, disaccharide, polysaccharide, alkylphosphate, acyloxyalkyl, alkylaminocarbonyl, alkoxyaralkyl and carboxyalkyl, wherein $R^3$ is optionally substituted at a substitutable position with one or more radicals independently selected at each occurrence from the group consisting of alkylcarbonyl, formyl, halo, alkyl, haloalkyl, oxo, cyano, nitro, carboxyl, alkoxy, aminocarbonyl, alkoxycarbonyl, carboxyalkyl, cyanoalkyl, hydroxyalkyl, haloalkylsulfonyloxy, alkoxyalkyloxyalkyl, carboxyalkoxyalkyl, cycloalkylalkyl, alkenyl, alkynyl, heterocyclyloxy, alkylthio, cycloalkyl, aryl, heterocyclyl, cycloalkenyl, aralkyl, heterocyclylalkyl, alkylthioalkyl, arylcarbonyl, aralkylcarbonyl, aralkenyl, alkoxyalkyl, arylthioalkyl, aryloxyalkyl, aralkylthioalkyl, aralkoxyalkyl, alkoxycarbonylalkyl, aminocarbonylalkyl, alkylaminocarbonyl, N-arylaminocarbonyl, N-alkyl-N-arylaminocarbonyl, alkylaminocarbonylalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, and N-alkyl-N-arylaminosulfonyl;

wherein at least one of $R^2$ and $R^3$ is other than hydrido;
wherein $R^2$ is other than alkyl, carboxyalkyl or alkylcarbonyl when $R^3$ is hydrido; and
wherein $R^3$ is other than alkyl, carboxyalkyl or alkylcarbonyl when $R^2$ is hydrido;
or, $R^2$ and $R^3$ are taken together along with the nitrogen to which they are attached to form a three to seven membered saturated, partially unsaturated or unsaturated heterocyclic ring and may optionally be substituted at a substitutable position with one or more $R^5$ radicals, wherein the $R^5$ radicals are independently selected at each occurrence from the group consisting of alkylcarbonyl, formyl, halo, alkyl, haloalkyl, alkylphosphate, phosphate, oxo, cyano, nitro, alkoxy, aminocarbonyl, alkoxycarbonyl, carboxyalkyl, cyanoalkyl, hydroxyalkyl, haloalkylsulfonyloxy, alkoxyalkyloxyalkyl, carboxyalkoxyalkyl, cycloalkylalkyl, alkenyl, alkynyl, heterocyclyloxy, alkylthio, cycloalkyl, aryl, heterocyclyl, cycloalkenyl, aralkyl, heterocyclylalkyl, alkylthioalkyl, arylcarbonyl, aralkylcarbonyl, aralkenyl, alkoxyalkyl, arylthioalkyl, aryloxyalkyl, aralkylthioalkyl, aralkoxyalkyl, alkoxycarbonylalkyl, aminocarbonylalkyl, alkylaminocarbonyl, N-arylaminocarbonyl, N-alkyl-N-arylaminocarbonyl, alkylaminocarbonylalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl and N-alkyl-N-arylaminosulfonyl; and $R^4$ is selected from hydrido and fluoro;

wherein $R^5$ is other than methyl when A is isoxazole, $R^1$ is phenyl and $R^2$ and $R^3$ are taken together to form a pyrrole ring.

The method of the present invention also includes prophylactic treatment. A preferred method of the invention is the administration of a compound of Formula (I) parenterally. In one embodiment, the compound of Formula (I) is administered intravenously. In another embodiment, the compound of Formula (I) is administered intramuscularly.

Also included in the family of compounds of Formula (I) are the stereoisomers thereof. Compounds of the present invention can possess one or more asymmetric carbon atoms and are thus capable of existing in the form of optical isomers as well as in the form of racemic or nonracemic mixtures thereof. Accordingly, some of the compounds of this invention may be present in racemic mixtures which are also included in this invention. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting an amine functionality of precursors to compounds of Formula (I) with an optically pure acid in an activated form or an optically pure isocyanate. Alternatively, diastereomeric derivatives can be prepared by reacting a carboxyl functionality of precursors to compounds of Formula I with an optically pure amine base. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

Also included in the family of compounds of Formula (I) are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula (I) may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclyl, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric and galacturonic acid. Suitable pharmaceutically-acceptable base addition salts of compounds of Formula (I) include metallic salts and organic salts. More preferred metallic salts include, but are not limited to appropriate alkali metal (group Ia) salts, alkaline earth metal (group IIa) salts and other physiological acceptable metals. Such salts can be made from aluminum, calcium, lithium, magnesium, potassium, sodium and zinc. Preferred organic salts can be made from tertiary amines and quanternary ammonium salts, including in part, trometamine, diethylamine, N,N'-dibenzylethylenediamine, chloroprocaine, choline, diethanolamine, ethylenediamine, meglumine (N-methylglucamine) and procaine. All of these salts may be prepared by conventional means from the corresponding compound of Formula (I) by reacting, for example, the appropriate acid or base with the compound of Formula (I).

General Synthetic Procedures

The cyclooxygenase-2 inhibitor prodrugs of the invention can be synthesized according to the following procedures of Schemes I–XVII, wherein the $R^1$–$R^8$ substituents are as defined for Formula (I), above, except where further noted.

Scheme I

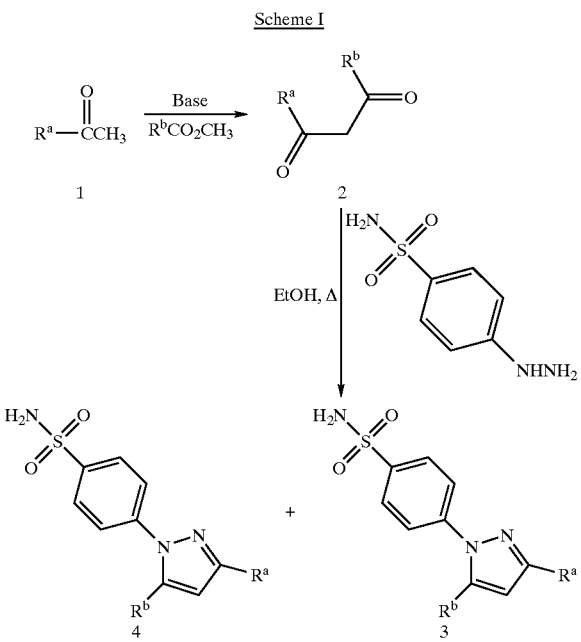

Synthetic Scheme I shows the preparation of cyclooxygenase-2 inhibitor compounds, as described in WO95/15316, which is incorporated herein by reference. In step 1, ketone 1 is treated with a base, preferably NaOMe or NaH, and an ester, or ester equivalent, to form the intermediate diketone 2 (in the enol form) which is used without further purification. In step 2, diketone 2 in an anhydrous protic solvent, such as absolute ethanol or acetic acid, is treated with the hydrochloride salt or the free base of a substituted hydrazine at reflux to afford a mixture of pyrazoles 3 and 4. Recrystallization or chromatography affords 3 usually as a solid. Similar pyrazoles can be prepared by methods described in U.S. Pat. Nos. 5,401,765, 5,434,178, 4,146,721, 5,051,518, 5,134,142 and 4,914,121 which also are incorporated herein by reference.

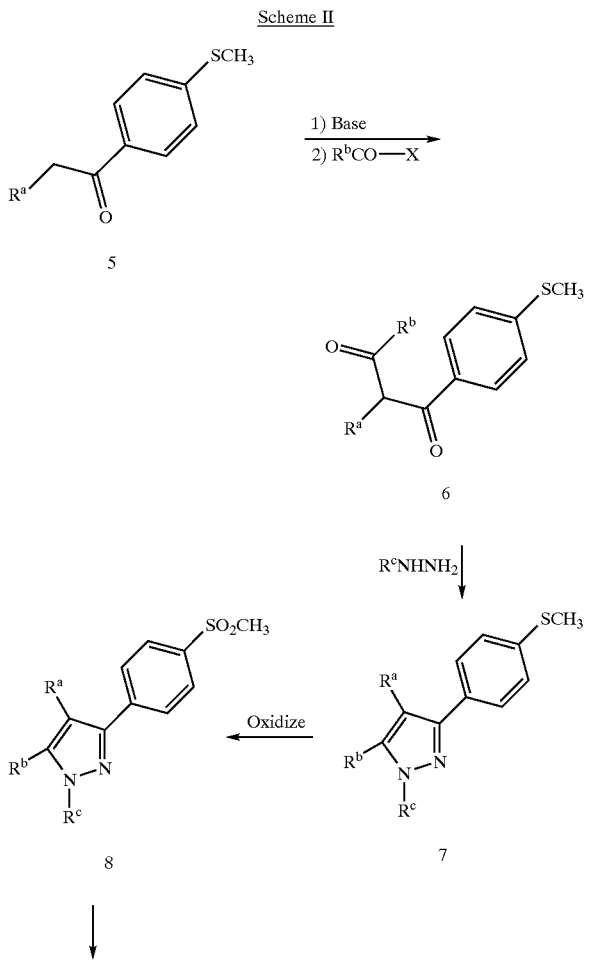

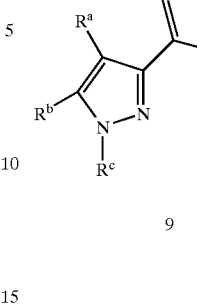

Scheme II shows the four step procedure for forming cyclooxygenase-2 inhibitor pyrazoles 8 as described in U.S. Pat. No. 5,486,534 (where $R^c$ is hydrido or alkyl) from ketones 5. In step 1, ketone 5 is reacted with a base, such as lithium bis(trimethylsilyl)amide or lithium diisopropylamide (LDA) to form the anion. In step 2, the anion is reacted with an acetylating reagent to provide diketone 6. In step 3, the reaction of diketone 6 with hydrazine or a substituted hydrazine, gives pyrazole 7. In step 4, the pyrazole 7 is oxidized with an oxidizing reagent, such as Oxone® (potassium peroxymonosulfate), 3-chloroperbenzoic acid (MCPBA) or hydrogen peroxide, to give a mixture of the desired 3-(alkylsulfonyl)phenyl-pyrazole 8 and the 5-(alkylsulfonyl)phenyl-pyrazole isomer. Sulfonamides 9 can be prepared such as by the Huang method [*Tet. Lett.*, 35, 7201–04 (1994)].

Alternatively, diketone 6 can be formed from ketone 5 by treatment with a base, such as sodium hydride, in a solvent, such as dimethylformamide, and further reacting with a nitrile to form an aminoketone. Treatment of the aminoketone with acid forms the diketone 6. Similar pyrazoles can be prepared by methods described in U.S. Pat. No. 3,984,431 which is incorporated herein by reference.

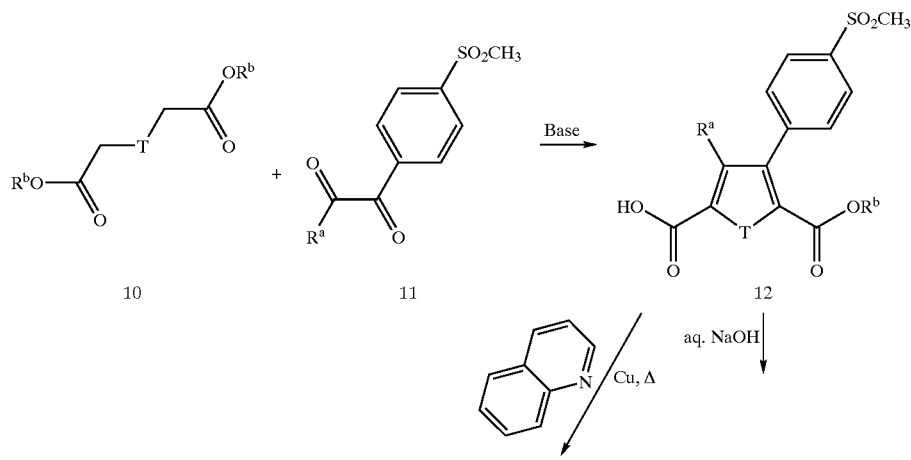

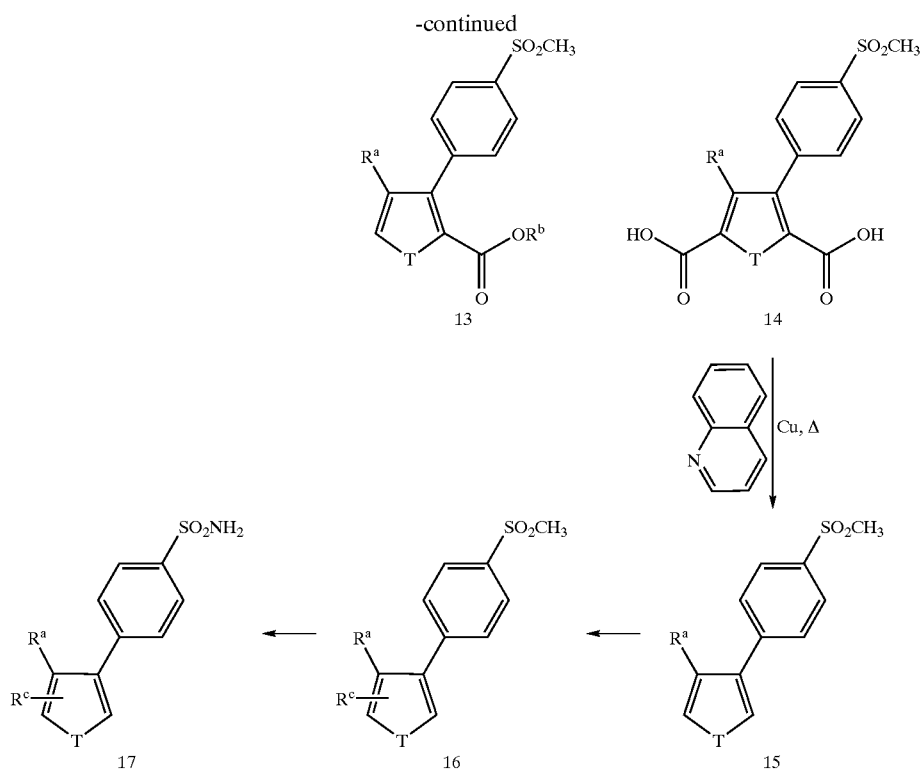
Cyclooxygenase-2 inhibitor diaryl/heteroaryl thiophenes (where T is S, and $R^b$ is alkyl) can be prepared by the methods described in U.S. Pat. Nos. 4,427,693, 4,302,461, 4,381,311, 4,590,205, and 4,820,827, and PCT documents WO 95/00501 and WO94/15932, which are incorporated herein by reference. Similar pyrroles (where T is N), furanones and furans (where T is O) can be prepared by methods described in PCT documents WO 95/00501 and WO94/15932.
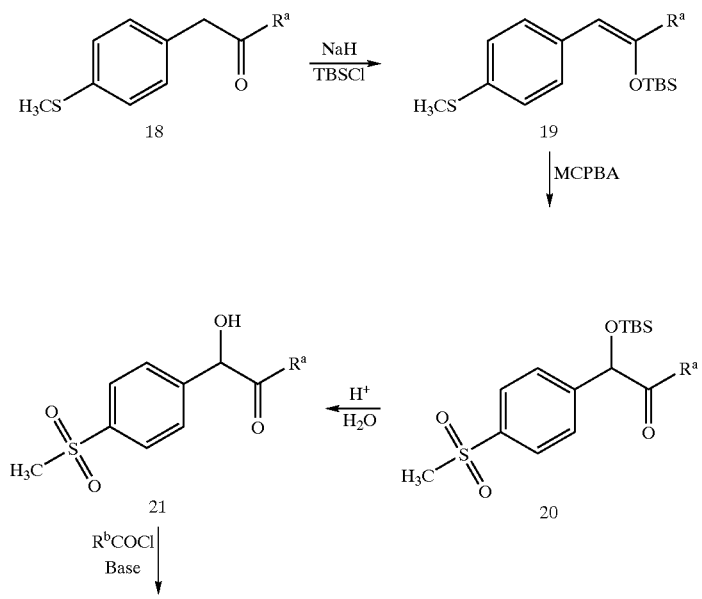

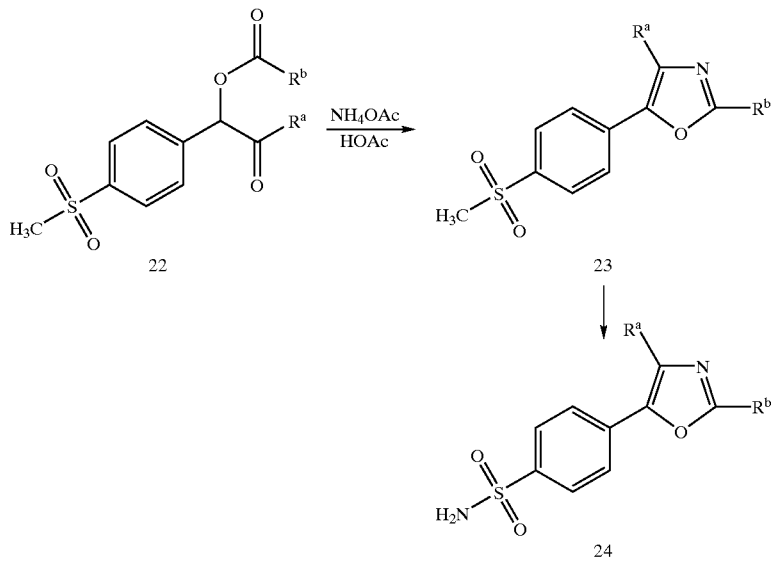

Cyclooxygenase-2 inhibitor diaryl/heteroaryl oxazoles can be prepared by the methods described in U.S. Pat. Nos. 5,380,738, 3,743,656, 3,644,499 and 3,647,858, and PCT documents WO 95/00501 and WO94/27980, which are incorporated herein by reference.

Scheme V

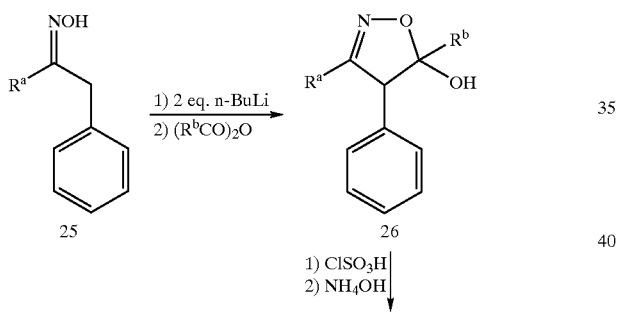

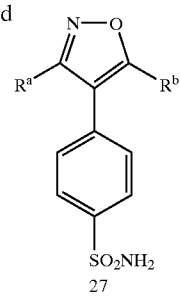

Cyclooxygenase-2 inhibitor diaryl/heteroaryl isoxazoles can be prepared by the methods described in PCT application Serial No. US96/01869, PCT documents WO92/05162, and WO92/19604, and European Publication EP 26928, which are incorporated herein by reference. Sulfonamides 27 can be formed from the hydrated isoxazole 26 in a two step procedure. First, hydrated isoxazole 26 is treated at about 0° C. with two or three equivalents of chlorosulfonic acid to form the corresponding sulfonyl chloride. In step two, the sulfonyl chloride thus formed is treated with concentrated ammonia to provide the sulfonamide derivative 27.

Scheme VI

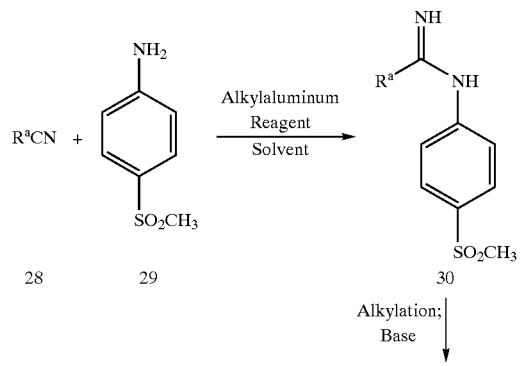

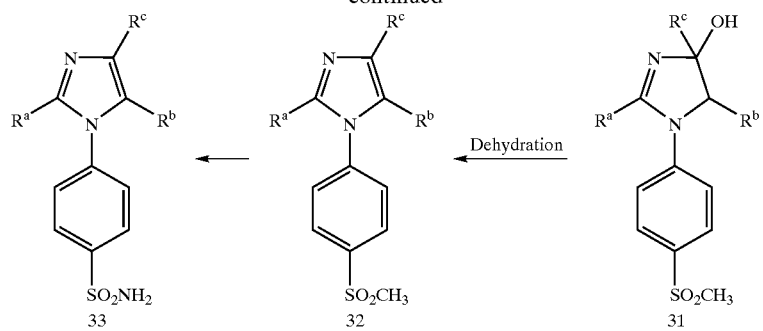

Scheme VI shows a three step preparation of the cyclooxygenase-2 inhibitor imidazoles 33. In step 1, the reaction of substituted nitriles ($R^aCN$) 28 with primary phenylamines 29 in the presence of alkylaluminum reagents such as trimethylaluminum, triethylaluminum, dimethylaluminum chloride, diethylaluminum chloride in the presence of inert solvents such as toluene, benzene, and xylene, gives amidines 30. In step 2, the reaction of amidine 30 with 2-haloketones (where X is Br or Cl) in the presence of bases, such as sodium bicarbonate, potassium carbonate, sodium carbonate, potassium bicarbonate or hindered tertiary amines such as N,N'-diisopropylethylamine, gives the 4,5-dihydroimidazoles 31 (where $R^b$ is alkyl). Some of the suitable solvents for this reaction are isopropanol, acetone and dimethylformamide. The reaction may be carried out at temperatures of about 20° C. to about 90° C. In step 3, the 4,5-dihydroimidazoles 31 may be dehydrated in the presence of an acid catalyst such as 4-toluenesulfonic acid or mineral acids to form the 1,2-disubstituted imidazoles 32 of the invention. Suitable solvents for this dehydration step are e.g., toluene, xylene and benzene. Trifluoroacetic acid can be used as solvent and catalyst for this dehydration step. Sulfonamides 33 can be prepared such as by the Huang method [*Tet. Lett.*, 35, 7201–04 (1994)].

In some cases (e.g., where $R^c$=methyl or phenyl) the intermediate 31 may not be readily isolable. The reaction, under the conditions described above, proceeds to give the targeted imidazoles directly.

Similarly, imidazoles can be prepared having the sulfonylphenyl moiety attached at position 2 and $R^a$ attached at the nitrogen atom at position 1. Diaryl/heteroarylimidazoles can be prepared by the methods described in U.S. Pat. No. 4,822,805 and PCT documents WO 93/14082 and WO96/03388, which are incorporated herein by reference.

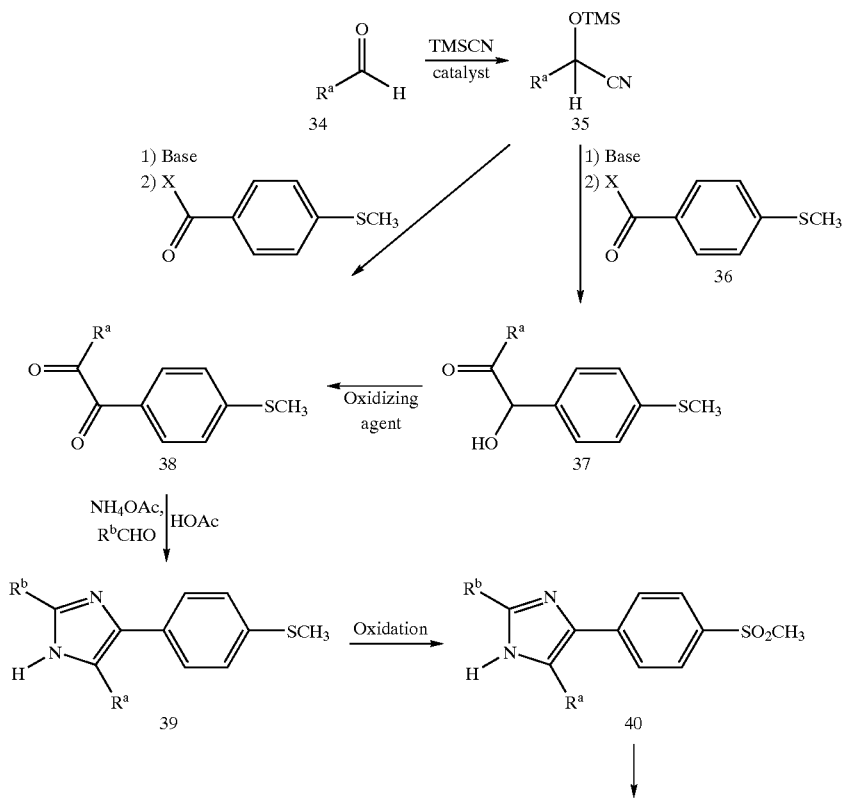

Scheme VII

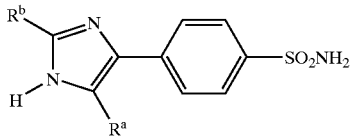

41

Imidazole cyclooxygenase-2 inhibitor compounds 41 may be synthesized according to the sequence outlined in Scheme VII. Aldehyde 34 may be converted to the protected cyanohydrin 35 by reaction with a trialkylsilyl cyanide, such as trimethylsilyl cyanide (TMSCN) in the presence of a catalyst such as zinc iodide (ZnI2) or potassium cyanide (KCN). Reaction of cyanohydrin 35 with a strong base followed by treatment with benzaldehyde 36 and using both acid and base treatments, in that order, on workup gives benzoin 37. Examples of strong bases suitable for this reaction are lithium diisopropylamide (LDA) and lithium hexamethyldisilazane. Benzoin 37 may be converted to benzil 38 by reaction with a suitable oxidizing agent, such as bismuth oxide or manganese dioxide, or by a Swern oxidation using dimethyl sulfoxide (DMSO) and trifluoroacetic anhydride. Benzil 38 may be obtained directly by reaction of the anion of cyanohydrin 35 with a substituted benzoic acid halide. Any of compounds 37 and 38 may be used as intermediates for conversion to imidazoles 39 according to chemical procedures known by those skilled in the art and described by M. R. Grimmett, "Advances in Imidazole Chemistry" in Advances in Heterocyclic Chemistry, 12, 104 (1970). The conversion of 38 to imidazoles 39 is carried out by reaction with ammonium acetate and an appropriate aldehyde ($R^b$CHO) in acetic acid. Benzoin 37 may be converted to imidazoles 39 by reaction with formamide. In addition, benzoin 37 may be converted to imidazoles by first acylating with an appropriate acyl group ($R^b$CO—) and then treating with ammonium hydroxide. Those skilled in the art will recognize that the oxidation of the sulfide to the sulfone may be carried out at any point along the way beginning with compounds 36, and including oxidation of imidazoles 39, using, for examples, reagents such as hydrogen peroxide in acetic acid, m-chloroperoxybenzoic acid (MCPBA) and potassium peroxymonosulfate (OXONE®). Sulfonamides 41 can be prepared such as by the Huang method [Tet. Lett., 35, 7201–04 (1994)].

Diaryl/heteroarylimidazoles can be prepared by the methods described in U.S. Pat. Nos. 3,707,475, 4,686,231, 4,503,065, 4,472,422, 4,372,964, 4,576,958, 3,901,908, PCT application Serial No. US95/09505, European publication EP 372,445, and PCT document WO 95/00501, which are incorporated herein by reference.

Scheme VIII

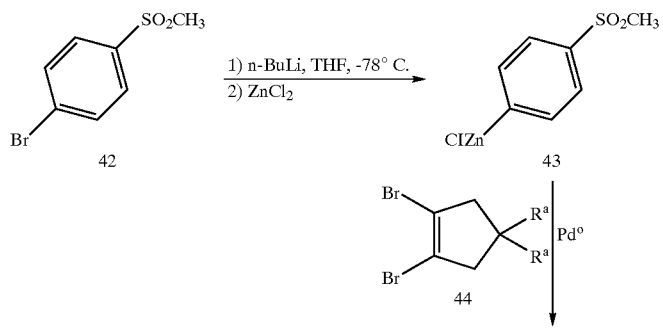

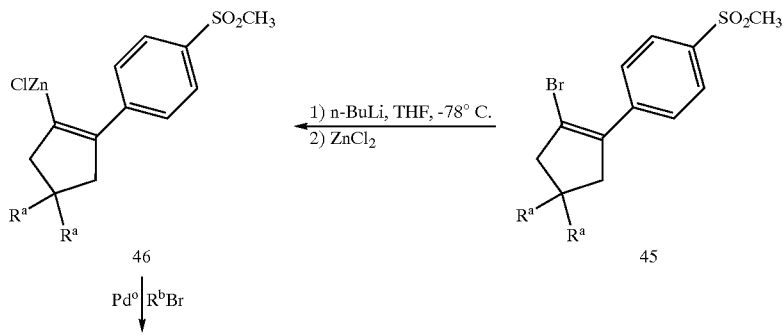

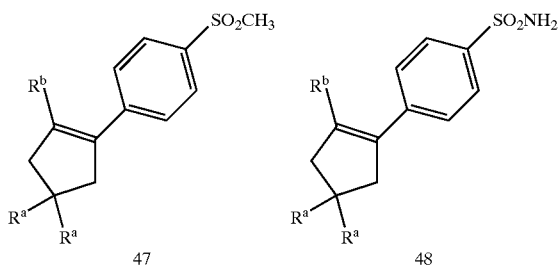

47    48

Diaryl/heteroaryl cyclopentene cyclooxygenase-2 inhibitors can be prepared by the methods described in U.S. Pat. No. 5,344,991, and PCT document WO 95/00501, which are incorporated herein by reference.

VIII) and the appropriate substituted phenylboronic acids. Using a coupling procedure similar to the one developed by Suzuki et al. [*Synth. Commun.*, 11, 513 (1981)], intermediates 49 are reacted with the boronic acids in toluene/ethanol Scheme IX

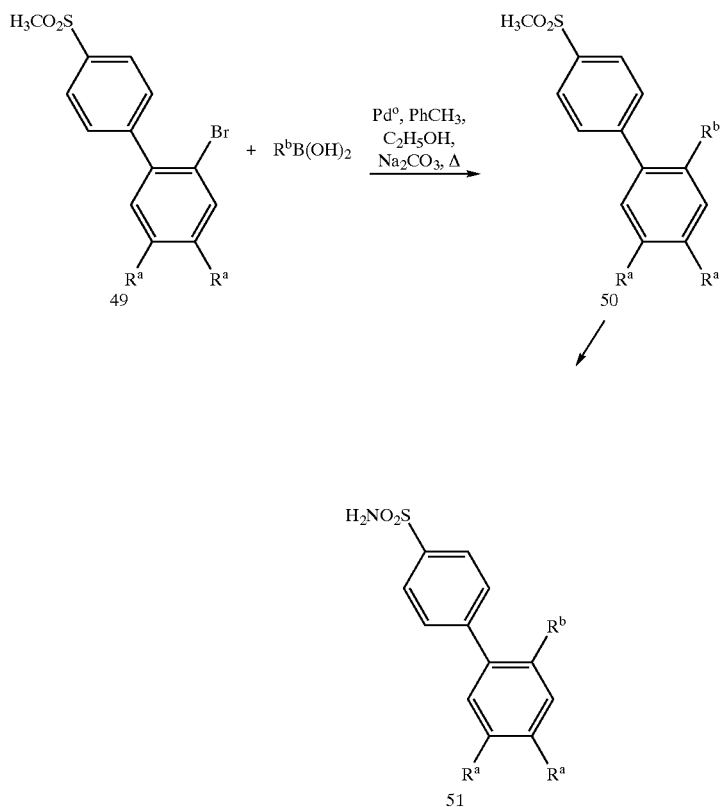

Similarly, Synthetic Scheme 1x shows the procedure for the preparation of 1,2-diarylbenzene cyclooxygenase-2 inhibitor agents 51 from 2-bromo-biphenyl intermediates 49 (prepared similar to that described in Synthetic Scheme VIII) and the appropriate substituted phenylboronic acids.

at reflux in the presence of a Pd° catalyst, e.g., tetrakis (triphenylphosphine)palladium(0), and 2M sodium carbonate to give the corresponding 1,2-diarylbenzene antiinflammatory agents 50 of this invention. Sulfonamides 51 can be prepared such as by the Huang method [*Tet. Lett.,* 35, 7201–04 (1994)]. Such terphenyl compounds can be prepared by the methods described in U.S. application Ser. No. 08/346,433, which is incorporated herein by reference.

treatment of an unsubstituted sulfonamide 56 with a suitable acylating agent such as an anhydride, acid chloride, acylimidazole, or active ester, in the presence of base and a suitable solvent, such as tetrahydrofuran (THF), to afford the Scheme X

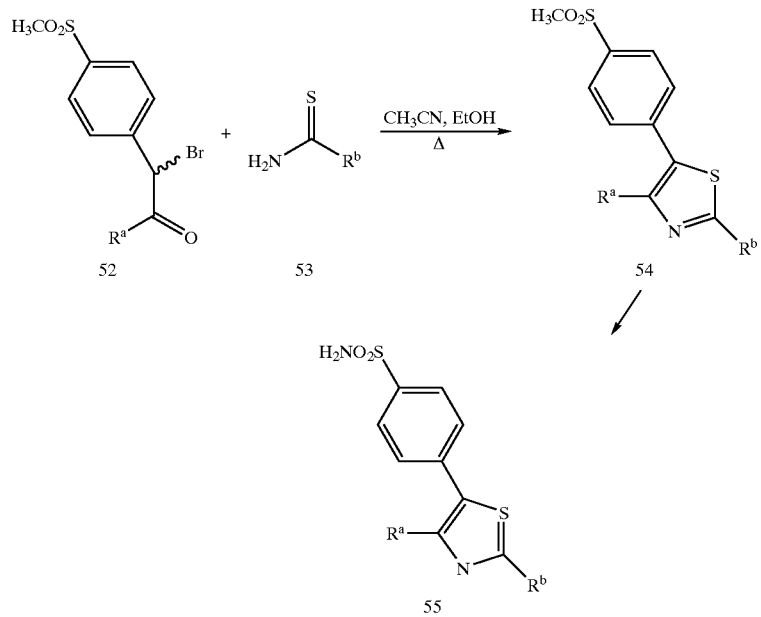

Diaryl/heteroaryl thiazole cyclooxygenase-2 inhibitors can be prepared by the methods described in U.S. Pat. Nos. 4,051,250, 4,632,930, European document EP 592,664, and PCT documents WO96/03392, and WO 95/00501, which are incorporated herein by reference. Isothiazoles can be prepared as described in PCT document WO 95/00501.

Diaryl/heteroaryl pyridine cyclooxygenase-2 inhibitors can be prepared by the methods described in U.S. Pat. Nos. 5,169,857, 4,011,328, 4,533,666, PCT application Serial No. US96/01110 and PCT application Serial No. US96/01111, which are incorporated herein by reference.

Scheme XI

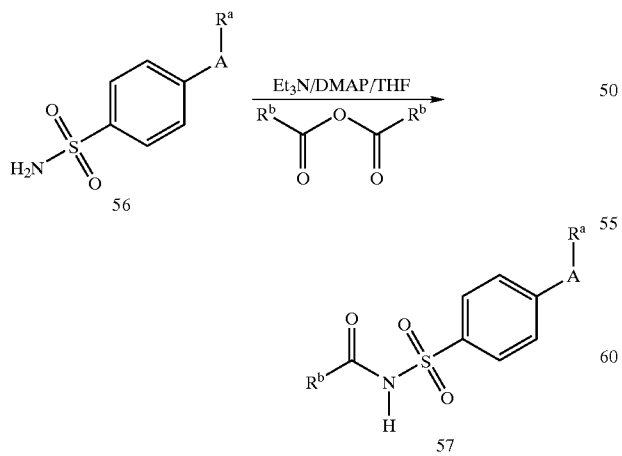

Synthetic Scheme XI illustrates a method for the preparation of acylated sulfonamides 57. The method involves acylated sulfonamide 57. The product 57 can then be isolated by chromatography or by crystallization.

Scheme XII

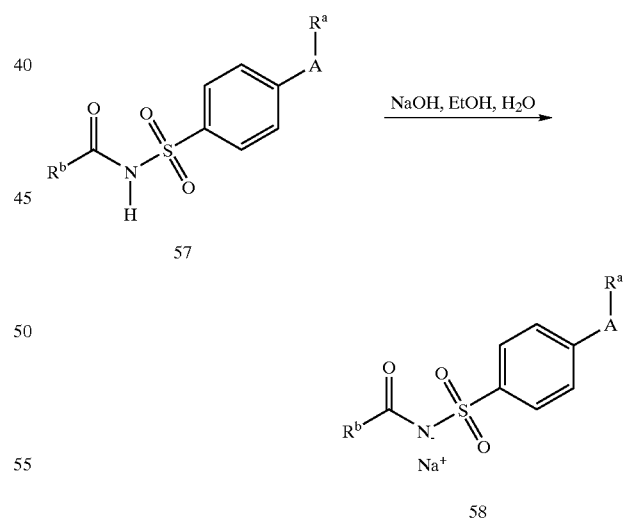

Synthetic Scheme XII shows the method for the preparation of the corresponding salt form of 57. Treatment of 57 with a suitable strong base such as sodium hydroxide, potassium hydroxide, calcium hydroxide and the like produces the corresponding salt form 58. A wide variety of solvents can be used so long as they do not react with the added strong base, such solvents as ethanol and tetrahydrofuran are preferred.

Scheme XIII

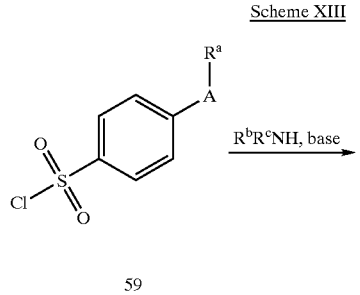

59

60

Synthetic Scheme XIII shows the method used for the preparation of substituted sulfonamides 60. The step involves treatment of a suitable sulfonyl chloride 59 with an amine to produce the substituted sulfonamide 59. The amine may be either a primary amine ($R^bNH_2$) or a secondary amine ($R^bR^cNH$). The reaction is generally conducted in the presence of added base. The reaction may also be conducted in the presence of excess amine. Under the conditions of excess amine, the amine functions as both nucleophile and base.

Scheme XIV

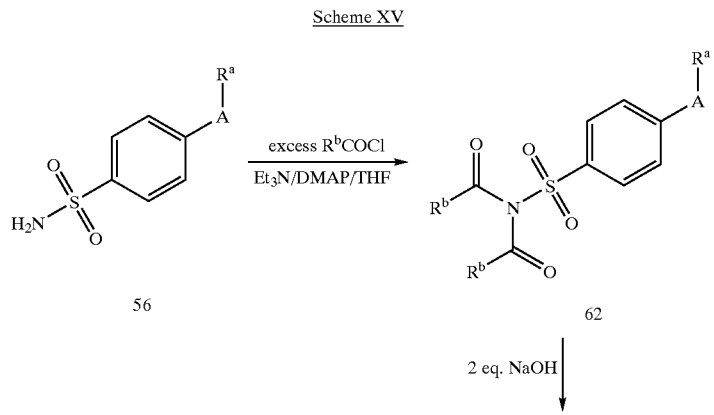

58

61

Synthetic Scheme XIV shows the method used for the synthesis of N-substituted acyl sulfonamides 61. The procedure involves treatment of the salt of an acylated sulfonamide 58 with an alkyl halide ($R^cX$) to produce the corresponding N-alkylated acyl sulfonamide 61. This process may be conducted in a wide variety of solvents with a wide array of electrophiles.

Scheme XV

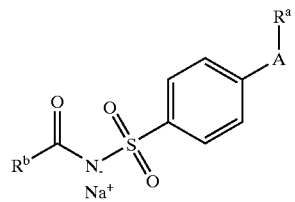

56

62

58

Synthetic Scheme XV illustrates the method used for the synthesis of certain N-acylated sulfonamides 57. The procedure involves treatment of the sulfonamide 56 with an excess of an anhydride, acid chloride or carbamyl chloride in the presence of a tertiary amine base to provide the corresponding bis(N-acylated)sulfonamide 62. The bis(N-acylated)sulfonamide 62 is then treated with two equivalents of a strong base such as sodium hydroxide to provide the sodium salt 58.

hol 65 is synthesized by following the literature procedure (*J. Org. Chem.* 57, 2195,1992). The alcohol 65 is oxidized such as by treatment with oxalyl chloride in an appropriate solvent, such as methylene chloride or DMSO. Addition, such as by Grignard reagents, produces the alcohol 67. Oxidation with pyridinium chlorochromate produces the ketones 68. Condensation with a [(N-substituted amino)

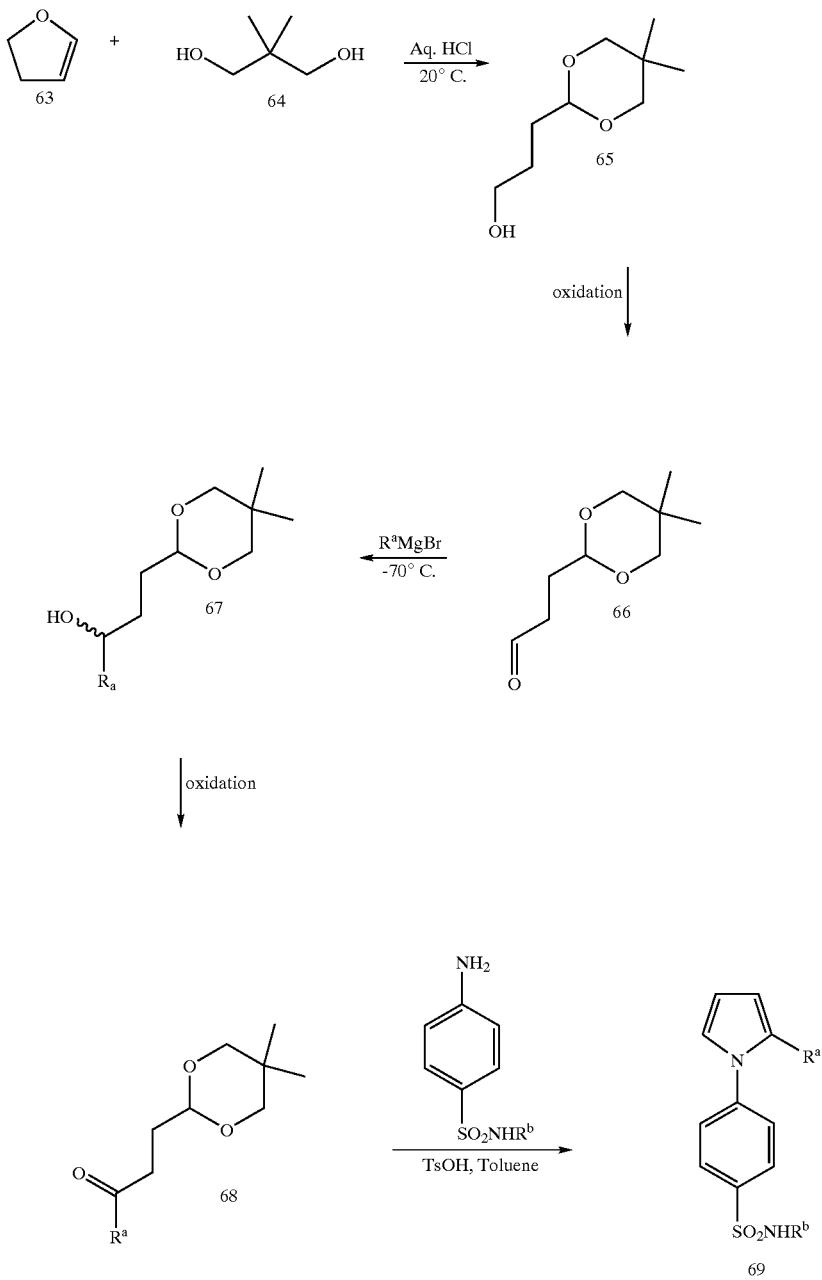

Scheme XVI

Synthetic Scheme XVI illustrates the method used for the synthesis of certain N-alkylated pyrrole sulfonamides. Alcohol sulfonyl]benzeneamine in the presence of p-toluenesulfonic acid (produces the substituted pyrrole sulfonamide 69.

Scheme XVII

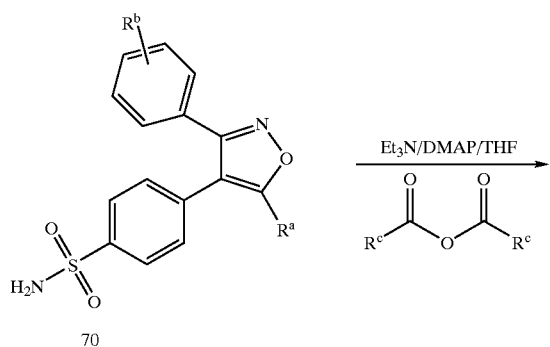

Synthetic Scheme XVII illustrates the method for the preparation of acylated isoxazole sulfonamides 71. The step involves treatment of an unsubstituted sulfonamide 70 with a suitable acylating agent such as an anhydride, acid chloride, acylimidazole, or active ester to afford the acylated sulfonamide 71. The product 71 can be isolated by chromatography or by crystallization.

Scheme XVIII

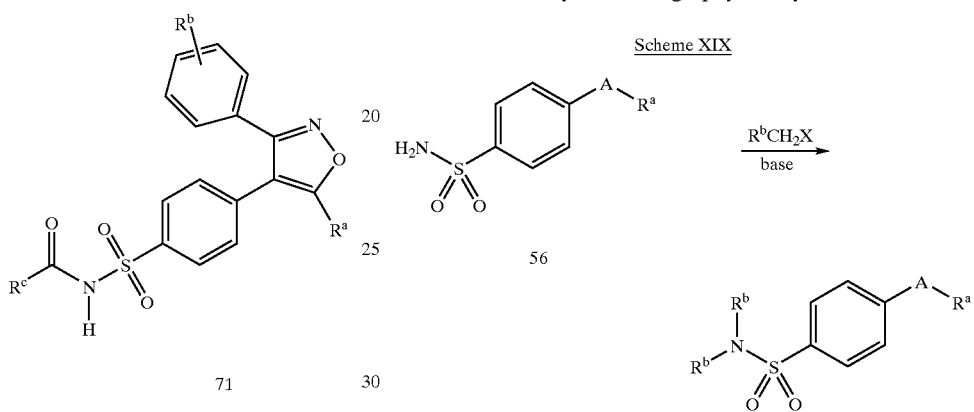

Synthetic Scheme XVIII illustrates a method for the preparation of N-substituted sulfonamides 72. The method involves acylation of the unsubstituted sulfonamide 56 with an acylating agent such as an anhydride, acid chloride, acyl imidazole, or active ester, in the presence of base and a suitable solvent such as tetrahydrofuran (THF). A catalyst such as dimethylaminopyridine (DMAP) may be added. The acylated sulfonamide 57 can be alkylated by treatment with an appropriate base and an alkylating agent such as an alkylhalide. The resulting N-acyl-N-alkylsulfonamide 61, upon treatment with an nucleophilic base such as hydroxide, a thiol, or an amine under appropriately basic conditions will yield an N—H—N-alkyl sulfonamide 72. The product 72 can be isolated by chromatography or crystallization.

Scheme XIX

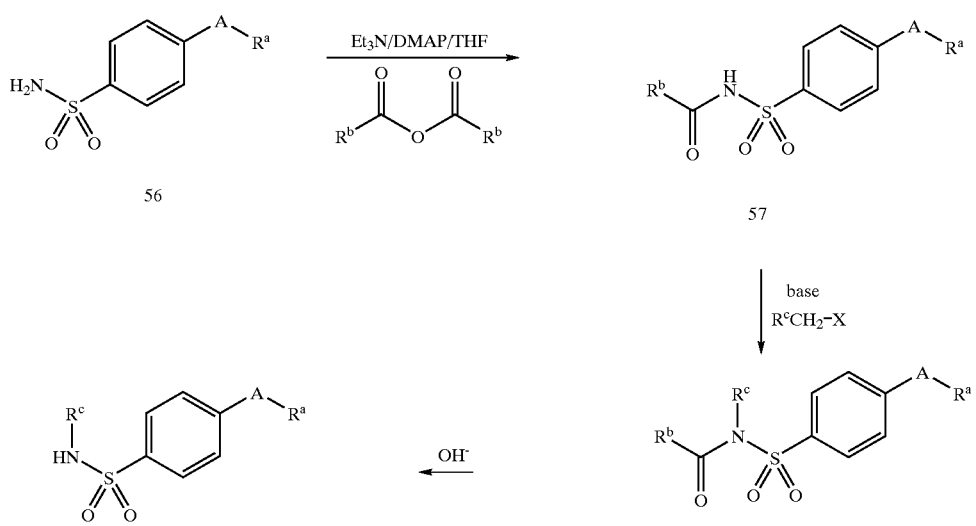

Synthetic Scheme XIX shows a direct alklyation of the sulfonamide 56 using an appropriate base such as sodium hydride with an aklylating agent such as an alkyl halide, aralkyl halide, an alkyl sulfonate, or a cyclic alkly sulfonate in an appropriate solvent such as dimethylformamide (DMF), dimthyl sulfoxide (DMSO), or tetrahydrofuran (THF). By choice of the appropriate conditions and number of equivalents of alkylating agent, the N-monoalkyl or N,N-dialkyl substitution can be obtained.

Scheme XX

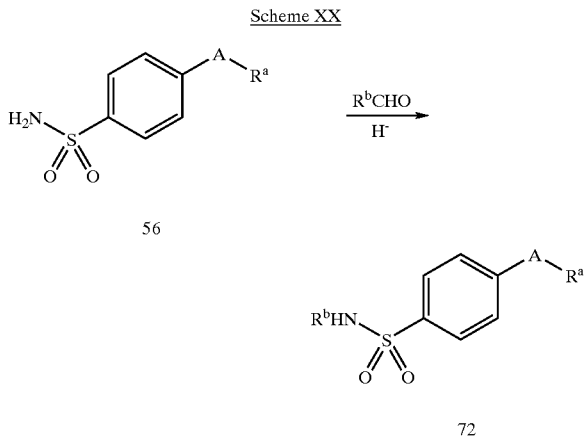

Scheme XX illustrates the reductive alkylation of sulfonamide 56 using an aldehyde, a hydride source such as sodium triacetoxyborohydride or sodium cyanoborohydridein and an appropriate solvent mixture which may include tetrahydrofuran and acetic acid or trifluoroacetic acid to form a N-alkyl or N-aryl sulfonamide 72.

Scheme XXI

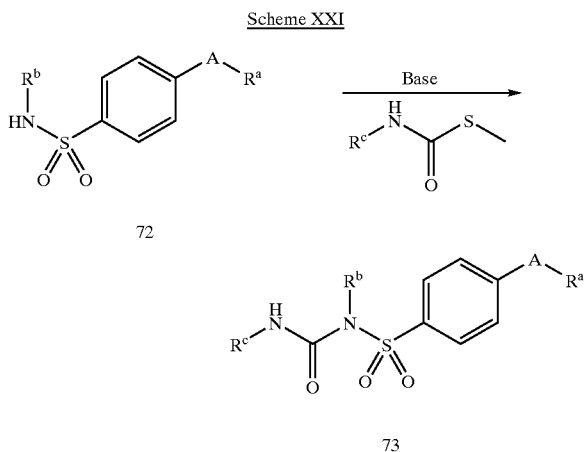

Scheme XXI shows the reaction of an primary or secondary sulfonamide 72, wherein $R^b$ must include H or alkyl, with an appropriate carbamoylating agent such as an N-alkyl-S-alkyl xanthate, N-aklyl-carbamoyl chloride or an n-alkyl isocyanate in the presence of a base such as triethylamine and optionally a catalyst such as dimethylaminopyridine (DMAP) in a solvent such as dimethyl formamide (DMF), dichloromethane (DCM), tetrahydrofuran (THF), or dimethyl sulfoxide (DMSO) to yield N-sulfonylcarbamate 73.

Scheme XXII

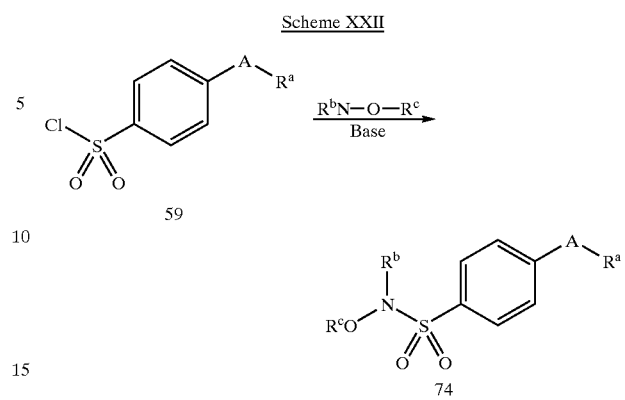

Scheme XXII illustrates the conversion of sulfonyl chloride 59 via its reaction with an appropriately substituted hydroxylamine, wherein $R^b$ must include H or alkyl and $R^c$ is either a protecting group or H, in the presence of a base such as triethyl amine in a solvent such as dimethyl formamide (DMF), dichloromethane (DCM), tetrahydrofuran (THF), or dimethyl sulfoxide (DMSO) to yield the substituted N-hydroxy sulfonamide 74. Where $R^c$ is a protecting group such as a tetrahydropyran (THP), it can be removed under acidic conditions such as by the treatment with toluenesulfonic acid in an appropriate solvent such as tetrahydrofuran with an alcohol or water present.

The following examples contain detailed descriptions of the methods of preparation of compounds of Formula (I). These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

The following abbreviations are used:
HCl—hydrochloric acid
DMSO—dimethylsulfoxide
DMSOd6—deuterated dimethylsulfoxide
$CDCl_3$—deuterated chloroform
$MgSO_4$—magnesium sulfate
$NaHCO_3$—sodium bicarbonate
$KHSO_4$—potassium hydrogen sulfate
DMF—dimethylformamide
NaOH—sodium hydroxide
BOC—tert-butyloxycarbonyl
$CD_3OD$—deuterated methanol
EtOH—ethanol
LiOH—lithium hydroxide
$CH_2Cl_2$—methylene chloride
h—hour
hr—hour
min—minutes
THF—tetrahydrofuran
TLC—thin layer chromatography
$Et_3N$—triethylamine
DBU—1,8-diazabicyclo[5.4.0]undec-7-ene
DMAP—4-dimethylaminopyridine

EXAMPLE 1

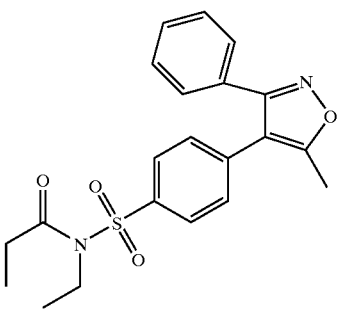

N-ethyl-4-(5-methyl-3-phenylisoxazol-4-yl)-N-propionylbenzenesulfonamide

N-ethyl-4-(5-methyl-3-phenylisoxazol-4-yl) benzenesulfonamide (5.0 g) and propionic anhydride (20 mL) were added together and heated to 50° C. at which point 20 µL of sulfuric acid was added. The temperature of the mixture was then increased to 80° C. and stirred for 15 minutes. The mixture was then cooled to 50° C. at a rate of 0.3° C./minute. If crystallization did not occur, then the mixture was cooled until crystallization was observed. The mixture was then held at 50° C. for 30 minutes followed by cooling to 0° C. at a rate of 0.3° C./minute. The mixture was held at 0° C. for about 30 minutes, filtered, washed with 10 mL MTBE at room temperature and vacuum dried for about 5 minutes. The washing procedure was repeated once again, and the product was then vacuum dried overnight at room temperature to provide N-ethyl-4-(5-methyl-3-phenylisoxazol-4-yl)-N-propionylbenzenesulfonamide (4.7 g).

EXAMPLE 2

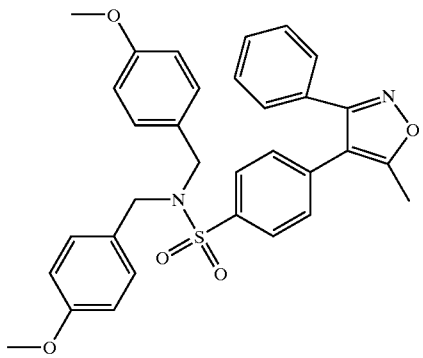

N,N-bis(4-methoxybenzyl)-4-(5-methyl-3-phenylisoxazol-4-yl)benzenesulfonamide

A mixture of 4-(5-methyl-3-phenyl-4-isoxazolyl) benzenesulfonamide (3.14 g, 0.01 mol) and potassium carbonate (5.53 g, 0.04 mol) in DMF (50 mL) was stirred at room temperature for 5 hours. 4-methylbenzylchloride (3.45 g, 0.022 mol) was then added and the resulting mixture was stirred overnight. Ethyl acetate (50 mL) and sat. water (100 mL) were then added and the layers were separated. The organic layer was washed with NaHCO3 (50 mL), brine, 1 N HCl (25 mL) and water (2×25 mL). Then the organic layer was then dried over MgSO$_4$, filtered and concentrated under vacuum. The resulting product was crystallized from boiling ethanol to afford 5.2 g of the product as a white solid: mp, 133.8–135.2° C.

EXAMPLE 3

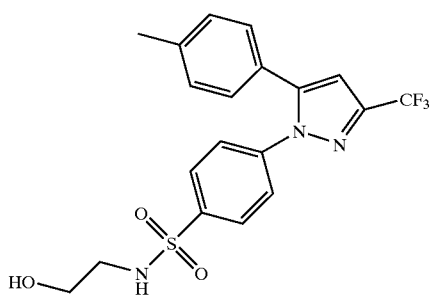

N-(2-hydroxyethyl)-4-[5-(4-methylphenyl)-3-(trifluoromethyl)-1H-pyrazol-1-yl]benzenesulfonamide Preparation of methyl N-(tert-butoxycarbonyl)-N-({4-[5-(4-methylphenyl)-3-(trifluoromethyl)-1H-pyrazol-1-yl] phenyl}sulfonyl)glycinate A mixture of celecoxib (1.00 g, 2.62 mmol), DMAP (0.160 g, (1.31 mmol), di-t-butyl dicarbonate (1.72 g, 7.87 mmol) and triethylamine (0.318 g, 3.14 mmol) in anhydrous THF (10.0 mL) was stirred at room temperature for 1 hour. Methyl bromoacetate (1.00 g, 6.55 mmol) and K$_2$CO$_3$ (0.724 g, 5.24 mmol) was then added and the resulting mixture was stirred at room temperature for 21.5 hours. The reaction mixture was poured into sat. NaHCO$_3$ and extracted with ethyl acetate (2×100 mL). The organic layers were combined, washed with sat. NaCl (50 mL), dried over MgSO$_4$, filtered and concentrated under vacuum. The resulting yellow glass was purified by flash chromatography (silica gel, 9:1 hexanes:ethyl acetate) to afford 1.32 g (91% yield) of the product as a white powder: mp, 88.5° C.; $^1$H NMR (dmso-d$_6$/300 MHz) δ 8.06 (d, 2H, J=8.7 Hz), 7.61 (d, 2H, J=8.9 Hz), 7.22–7.16 (m, 5H), 4.59 (s, 2H), 3.69 (s, 3H), 2.30 (s, 3H), 1.23 (s, 9H); HRMS (M+H)$^+$ calcd. for C$_{25}$H$_{27}$F$_3$O$_6$S: 554.1573; found: 554.1601.

Preparation of N-(2-hydroxyethyl)-4-[5-(4-methylphenyl)-3-(trifluoromethyl)-1H-pyrazol-1-yl]benzenesulfonamide To a solution of methyl N-(tert-butoxycarbonyl)-N-({4-[5-(4-methylphenyl)-3-(trifluoromethyl)-1H-pyrazol-1-yl] phenyl}sulfonyl)glycinate (1.18 g, 2.13 mmol) in 50 ml anhydrous methanol (50 mL) was added NaBH$_4$ (0.8 g, 21.1 mmol) and the mixture was stirred at room temperature. At 30 minutes, additional MeOH (50 mL) was added and then NaBH$_4$ (3.6 g, 95.1 mmol) was added in portions over 5.5 hours and the mixture was stirred at room temperature for an additional 18 hours. The solvent was removed under vacuum and ethyl acetate (100 mL) was added. The mixture was then poured into sat. NaHCO$_3$ (200 mL) and the layers were separated. The aqueous layer was then extracted with ethyl acetate (100 mL). The organic layers were combined, washed with sat. NaHCO$_3$ (100 mL), dried over MgSO$_4$, filtered and concentrated under vacuum. The resulting pale yellow glass was dissolved in TFA (100 mL) and the mixture was allowed to stand at room temperature for 2 hours. The TFA was removed under vacuum, and remaining traces of TFA were removed by addition and removal under vacuum of CH$_2$Cl$_2$ (several portions) to give a yellow oil. The crude product was purified by flash chromatography (silica gel, 1:1 hexanes:ethyl acetate) to afford 0.365 g (40% yield) of the product as a white powder: mp, 57.8° C.; $^1$H NMR (dmsod$_6$/300 MHz) δ 7.86–7.83 (m, 2H), 7.76 (exchangeable with D$_2$O, t, 1H), J=5.9 Hz), 7.56–7.53 (m, 2H), 7.22–7.17 (m, 5H), 4.70 (exchangeable with D$_2$O, t, 1H, J=5.6 Hz), 3.37–3.32 (m, 2H), 2.84–2.79 (m, 2H), 2.30 (s 3H); HRMS (M+H)$^+$ calcd. for C$_{19}$H$_{19}$F$_3$N$_3$O$_3$S: 426.1099; found 426.1071.

EXAMPLE 4

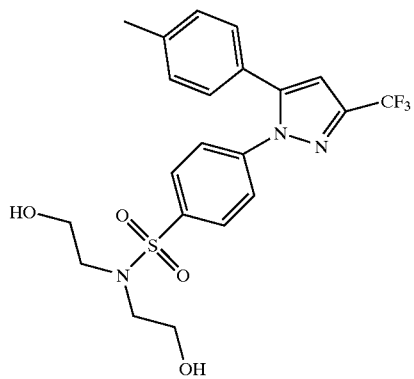

N,N-bis(2-hydroxyethyl)-4-[5-(4-methylphenyl)-3-(trifluoromethyl)-1H-pyrazol-1-yl] benzenesulfonamide Preparation of methyl N-(2-methoxy-2-oxoethyl)-N-({4-[5-(4-methylphenyl)-3-(trifluoromethyl)-1H-pyrazol-1-yl] phenyl}sulfonyl)glycinate A mixture of Celecoxib (0.500 g, 1.31 mmol), methyl bromoacetate (0.501 g, 3.28 mmol) and K$_2$CO$_3$ (0.362 g, 2.62 mmol) in anhydrous DMF (5.0 mL) was stirred at room temperature for 21 hours. The mixture was then poured into sat. NaHCO$_3$ (200 mL) and extracted with ethyl acetate (200 mL). The ethyl acetate solution was then washed with sat NaCl (50 mL), dried over MgSO$_4$, filtered and concentrated under vacuum. The crude product was purified by flash chromatography (silica gel, 98:2 methylene chloride:methanol) to afford 0.350 g (51% yield) of the product as a colorless glass: $^1$H NMR (dmso-d$_6$/300 MHz) δ 7.90 (d, 2H, J=8.7 Hz), 7.53 (d, 2H, J=8.7 Hz), 7.23–7.17 (m, 5H), 4.19 (s, 4H), 3.54 (s, 6H), 2.30 (s, 3H); HRMS (M+NH$_4$)$^+$ calcd. for C$_{23}$H$_{26}$F$_3$N$_4$O$_6$S: 543.1525; found: 543.1526.

Preparation of N,N-bis(2-hydroxyethyl)-4-[5-(4-methylphenyl)-3-(trifluoromethyl)-1H-pyrazol-1-yl] benzenesulfonamide To a solution of methyl N-(2-methoxy-2-oxoethyl)-N-({4-[5-(4-methylphenyl)-3-(trifluoromethyl)-1H-pyrazol-1-yl]phenyl}sulfonyl)glycinate prepared as in example 2.A. (0.330 g, 0.628 mmol) in anhydrous methanol (50 mL), was added NaBH$_4$ (0.4 g, 10.6 mmol) and the mixture was allowed to stand at room temperature for 2 hours. Additional NaBH$_4$ (0.4 g, 10.6 mmol) was then added and after 1 hour, the solvent was removed in vacuo. The residue was dissolved in water (100 mL), saturated with NaCl and the pH was adjusted to 2 with 1N HCl. The solution was extracted with ethyl acetate (200 mL). The organic solution was washed with sat. NaCl (50 mL), dried over MgSO$_4$, filtered and concentrated under vacuum to afford 0.285 g (97% yield) of the product as a white powder: mp, 79.1° C.; $^1$H NMR (dmso-d$_6$/300 MHz) δ 7.87 (d, 2H, J=8.7 Hz), 7.54 (d, 2H, J=8.7 Hz), 7.23–7.16 (m, 5H), 4.81 (exchangeable with D$_2$O, t, 2H, J=5.4 Hz), 3.52–3.46 (m, 4H), 3.20 (t, 4H, J=6.0 Hz), 2.30 (s, 3H); HRMS (M+H)$^+$ calcd. for C$_{21}$H$_{23}$F$_3$N$_3$O$_4$S: 470.1361; found 470.1330.

Biological Evaluation

Air-Pouch Model of Inflammation

Male Lewis rats (175–200 g) were used. Air cavities were produced by subcutaneous injection of 20 mL of sterile air into the intrascapular area of the back. An additional 10 mL of air was injected into the cavity every 3 days to keep the space open. Seven days after the initial air injection, 2 mL of a 1% solution of carrageenan (Sigma) dissolved in saline was injected directly into the pouch to produce an inflammatory response. The volume of exudate was measured with a Coulter Counter. The differential cell count was determined by Wright-Giemsa staining. PGE$_2$ and 6-keto-PGF$_{1\alpha}$, were determined in the pouch exudates by specific ELISAs (Cayman Chemicals, Ann Arbor, Mich.). Results are shown in Table I.

TABLE I

| Example | AIR POUCH TEST % Inhibition @ 20 mg/kg body weight |
|---------|------------------------------------------------------|
| 3       | 59                                                   |
| 4       | 10                                                   |

Also embraced within this invention is a class of pharmaceutical compositions comprising the active compounds of this combination therapy in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly (IV), intraperitoneally, subcutaneously, intramuscularly (IM) or topically.

For oral administration, the pharmaceutical composition may be in the form of, for example, a tablet, hard or soft capsule, lozenges, dispensable powders, suspension or liquid. The pharmaceutical composition is preferably made in the form of a dosage unit containing a particular amount of the active ingredient. Examples of such dosage units are tablets or capsules.

The active ingredient may also be administered by injection (IV, IM, subcutaneous or jet) as a composition wherein, for example, saline, dextrose, or water may be used as a suitable carrier. The pH of the composition may be adjusted, if necessary, with suitable acid, base, or buffer. Suitable bulking, dispersing, wetting or suspending agents, including mannitol and PEG 400, may also be included in the composition. A suitable parenteral composition can also include a compound formulated as a sterile solid substance, including lyophilized powder, in injection vials. Aqueous solution can be added to dissolve the compound prior to injection.

The amount of therapeutically active compounds that are administered and the dosage regimen for treating a disease condition with the compounds and/or compositions of this invention depends on a variety of factors, including the age, weight, sex and medical condition of the subject, the severity of the inflammation or inflammation related disorder, the route and frequency of administration, and the particular compound employed, and thus may vary widely. The prodrug compositions should include similar dosages as for the parent compounds. The pharmaceutical compositions may contain active ingredients in the range of about 0.1 to 1000 mg, preferably in the range of about 0.5 to 250 mg and most preferably between about 1 and 60 mg. A daily dose of about 0.01 to 100 mg/kg body weight, preferably between about 0.05 and about 20 mg/kg body weight and most preferably between about 0.1 to 10 mg/kg body weight, may be appropriate. The daily dose can be administered in one to four doses per day.

In the case of skin conditions, it may be preferable to apply a topical preparation of compounds of this invention to the affected area two to four times a day.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, iso-propyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of formula:

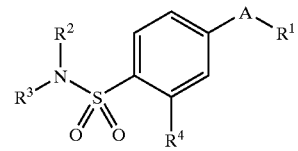

(I)

or a pharmaceutically-acceptable salt thereof wherein:

A is a pyrazole group optionally substituted at a substitutable position with one or more radicals independently selected at each occurrence from the group consisting of alkylcarbonyl, formyl, halo, alkyl, haloalkyl, oxo, cyano, intro, carboxyl, alkoxy, aminocarbonyl, alkoxycarbonyl, carboxyalkyl, cyanoalkyl, hydroxyalkyl, haloalkylsulonyloxy, alkoxyalkyloxyalkyl, carboxyalkoxyalkyl, alkenyl, alkynyl, alkylthio, alkylthioalkyl, alkoxyalkyl, alkoxycarbonylalkyl, aminocarbonylalkyl, alkylaminocarbonyl, alkylaminocarbonylalkyl, alkylamino, aminoalkyl, alkylaminoalkyl, alkylsutfinyl, alkylsulfonyl, aminosulfonyl, and alkylaminosulfonyl;

$R^1$ is a phenyl group optionally substituted at a substitutable position with one or more radicals independently selected at each occurrence from the group consisting of alkyl, haloalkyl, cyano, carboxyl, alkoxycarbonyl, hydroxyl, hydroxyalkyl, haloalkoxy, amino, alkylamino, nitro, alkoxyalkyl, alkylsulfinyl, halo, alkoxy, and alkylthio;

$R^2$ and $R^3$ are independently selected from the group consisting of hydroxyalkyl and hydrido but at least one of $R^2$ and $R^3$ is other than hydrido; and $R^4$ is selected from the group consisting of hydrido and fluoro.

2. The compound of claim 1 wherein $R^1$ is a phenyl group optionally substituted at a substitutable position with one or more radicals independently selected at each occurrence from the group consisting of lower alkyl, lower haloalkyl, cyano, carboxyl, lower alkoxycarbonyl, hydroxyl, lower hydroxyalkyl, lower haloalkoxy, amino, lower alkylamino, nitro, lower alkoxyalkyl, lower alkylsulfinyl, halo, lower alkoxy and lower alkylthio.

3. The compound of claim 1 wherein $R^1$ is a phenyl group optionally substituted at a substitutable position with one or more radicals independently selected at each occurrence from the group consisting of methyl, trifluoromethyl, hydroxyl, hydroxymethyl, trifluoromethoxy, intro, methoxymethyl, fluoro, chloro, bromo, methoxy and methylthio.

4. The compound of claim 1 having formula:

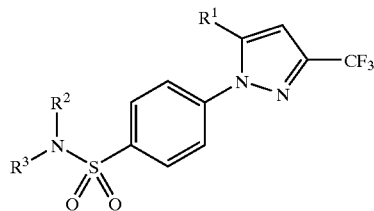

or a pharmaceutically-acceptable salt thereof wherein:

$R^1$ is p-tolyl; $R^2$ is —$CH_2OH$; and $R^3$ is —$CH_2OH$; or
$R^1$ is p-tolyl; $R^2$ is —H; and $R^3$ is —$CH_2OH$; or
$R^1$ is p-tolyl; $R^2$ is —H; and $R^3$ is —$CH_2CH_2OH$; or
$R^1$ is p-tolyl; $R^2$ is —$CH_2CH_2OH$; and $R^3$ is —$CH_2CH_2OH$.

5. A compound which is N-(2-hydroxyethyl)-4-[5-(4-methylphenyl)-3-(trifluoromethyl)-1H-pyrazol-1-yl]benzenesulfonamide, or a pharmaceuticaly-acceptable salt thereof.

6. A compound which is N,N-bis(2-hydroxyethyl)-4-[5-(4-methylphenyl)-3-(trifluoromethyl)-1H-pyrazol-1-yl]benzenesulfonamide, or a pharmaceuticaly-acceptable salt thereof.

7. The compound of claim 1 that is a pharmaceutically-acceptable metal salt.

8. The compound of claim 7 wherein the metal salt is an alkali metal salt or an alkaline earth metal salt.

9. The compound of claim 7 wherein the metal salt is selected from the consisting of sodium and potassium salts.

10. A pharmaceutical composition comprising a therapeutically-effective amount of a compound of claim 1 and at least one carrier material.

11. The composition of claim 10 wherein the compound is N-(2-hydroxyethyl)-4-[5-(4-methylphenyl)-3-(trifluoromethyl)-1H-pyrazol-1-yl]benzenesulfonamide, or a pharmaceutically-acceptable salt thereof.

12. The composition of claim 10 wherein the compound is N,N-bis(2-hydroxyethyl)-4-[5-(4-methylphenyl)-3-(trifluoromethyl)-1H-pyrazol-1-yl]benzenesulfonamide, or a pharmaceutically-acceptable salt thereof.

* * * * *